US012064405B2

United States Patent
Lee et al.

(10) Patent No.: US 12,064,405 B2
(45) Date of Patent: Aug. 20, 2024

(54) IMMUNOSUPPRESSANT COMPRISING TSAHC OR A PHARMACEUTICALLY ACCEPTABLE SALTS THEREOF AS AN ACTIVE INGREDIENT

(71) Applicant: Seoul National University R&DB Foundation, Seoul (KR)

(72) Inventors: Jung Weon Lee, Seoul (KR); Eunmi Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 235 days.

(21) Appl. No.: 17/520,499

(22) Filed: Nov. 5, 2021

(65) Prior Publication Data
US 2022/0160663 A1  May 26, 2022

(30) Foreign Application Priority Data
Nov. 6, 2020  (KR) .................. 10-2020-0148087

(51) Int. Cl.
*A61K 31/18*   (2006.01)
*A61P 1/16*    (2006.01)
*A61P 37/06*   (2006.01)

(52) U.S. Cl.
CPC ............... *A61K 31/18* (2013.01); *A61P 1/16* (2018.01); *A61P 37/06* (2018.01)

(58) Field of Classification Search
CPC ...................................................... A61K 31/18
See application file for complete search history.

(56) References Cited

FOREIGN PATENT DOCUMENTS

| KR | 10-0751899 | 8/2007 | |
| KR | 10-2008-0052391 | 6/2008 | |
| KR | 10-2012-0023524 | 3/2012 | |
| KR | 10-2019-0046705 | 5/2019 | |
| WO | WO2019124608 A1 * | 6/2019 | ............ A61K 31/18 |

OTHER PUBLICATIONS

Min-Gyu Jeon et al. Inflammation, vol. 40, No. 6, Dec. 2017.*

* cited by examiner

*Primary Examiner* — Paul V Ward
(74) *Attorney, Agent, or Firm* — Fredrikson & Byron, P.A.

(57) ABSTRACT

The present invention relates to an immunosuppressant comprising TSAHC or a pharmaceutically acceptable salt thereof as an active ingredient. TSAHC treatment suppressed the expression and secretion of cytokines/chemokines such as IL6, IL1β, TNFα, CXCL1, CXCL2, CXCL3, CXCL6, CXCL8, CCL2, CCL5, CCL20, CXCL10 and CCR10 according to the expression of TM4SF5 gene and protein, and the cytokines or chemokines mediated by the expression of TM4SF5 induced abnormalities in the inflammatory response and metabolic function of liver tissues, hepatic epithelial cells and macrophages, and correlated with liver tissue damage and immune cell recruit in TM4SF5 transgenic animals. Therefore, a composition comprising TSAHC or a pharmaceutically acceptable salt thereof as an active ingredient can be effectively used as an immunosuppressant.

12 Claims, 26 Drawing Sheets
Specification includes a Sequence Listing.

Forward primer:CMV-F1
5'CGC TAT TAC CAT GGT GAT GCG 3'
(SEQ ID NO:91)
Reverse primer:TM4SF5-R1
5'AGA CAC CGA GAG GCA GTA GAT 3'
(SEQ ID NO:92)

NO:no template
N/C:normal mouse genomic DNA
P/C:positive(plasmid DNA) control

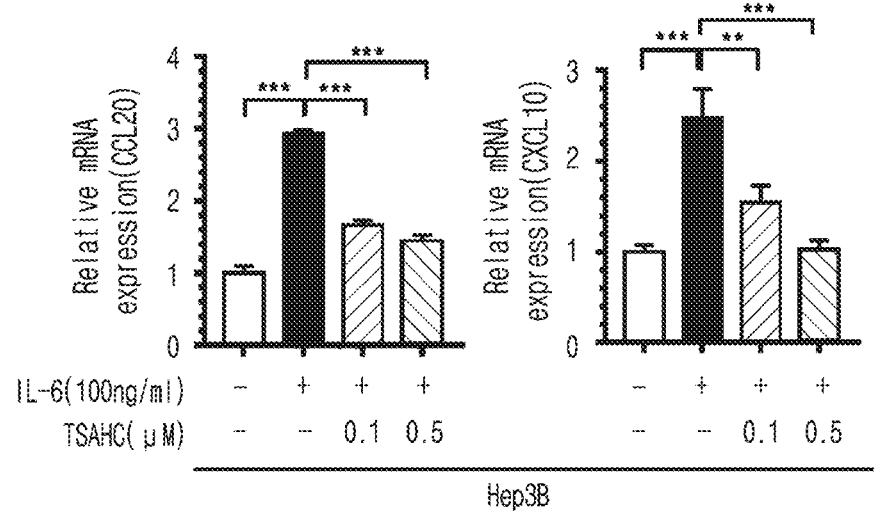

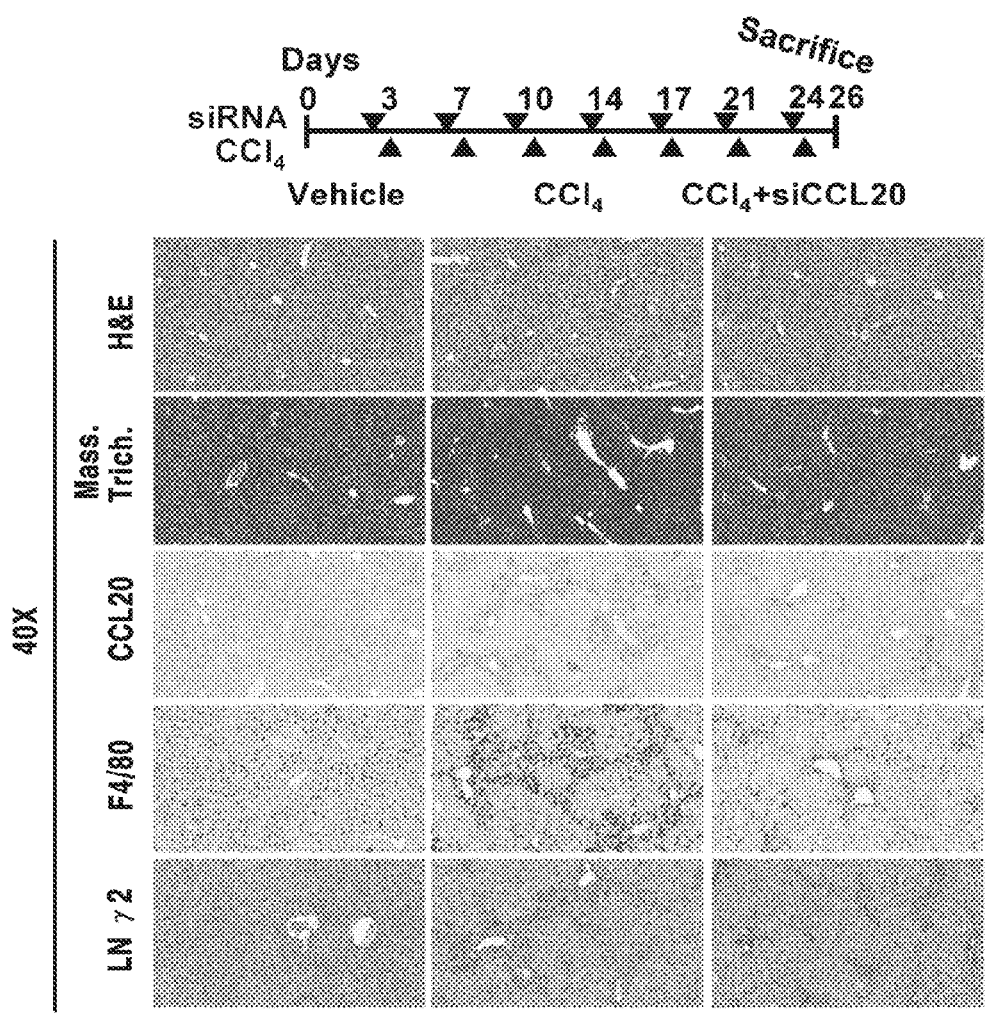

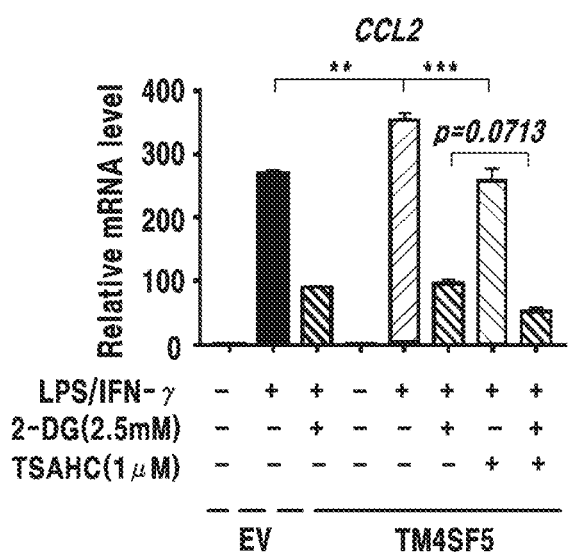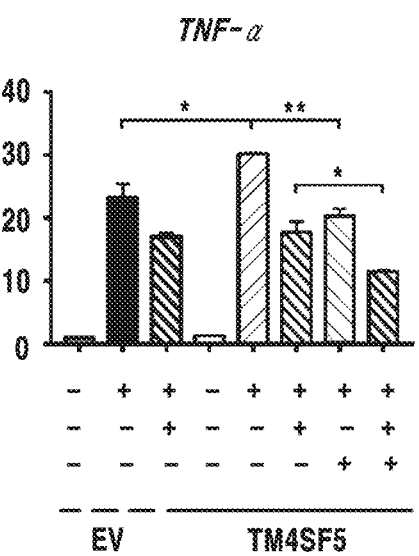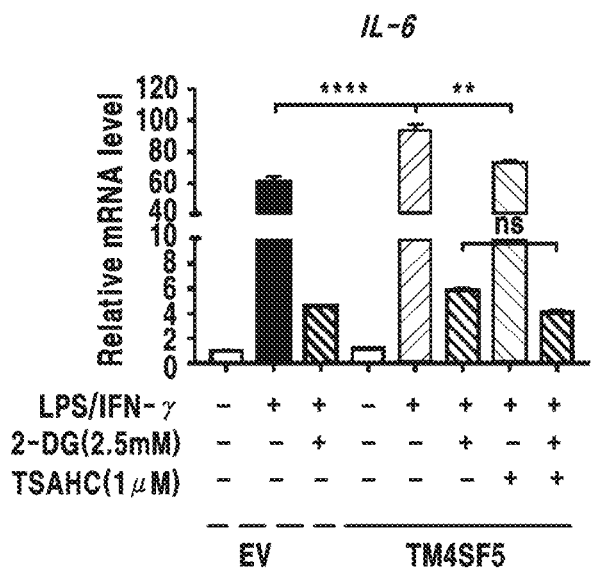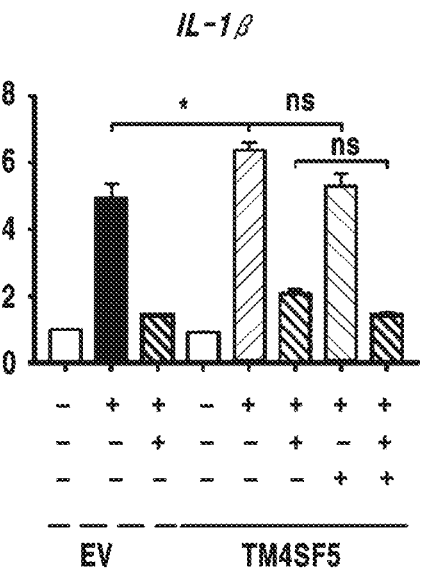

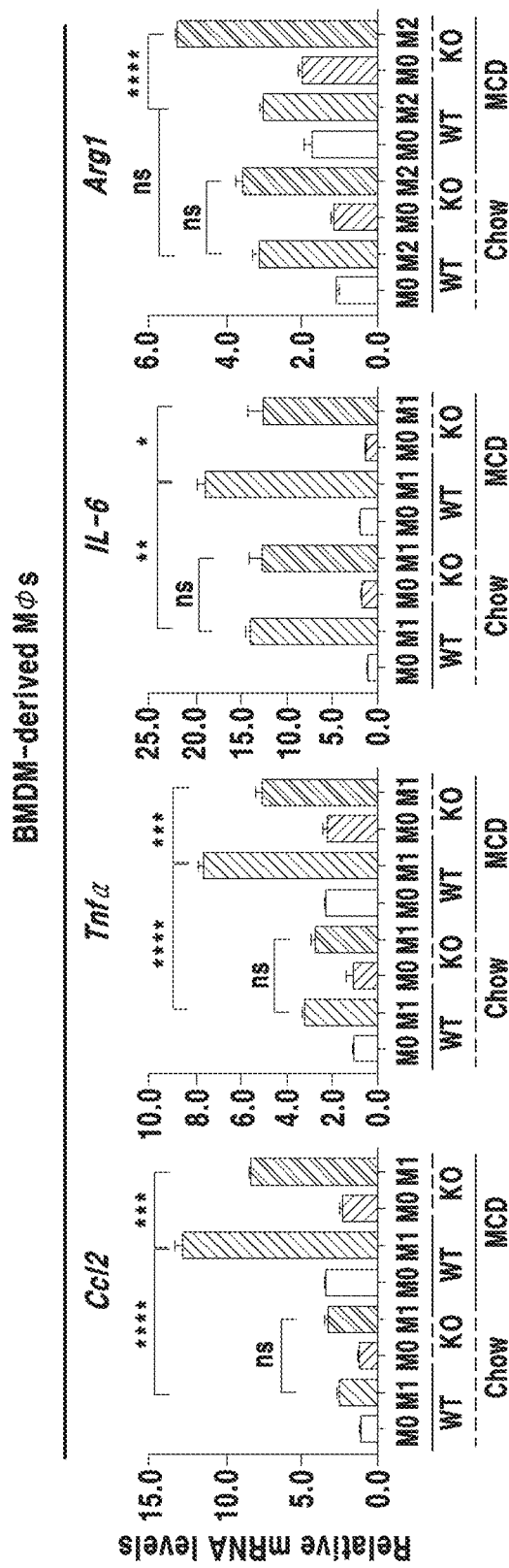

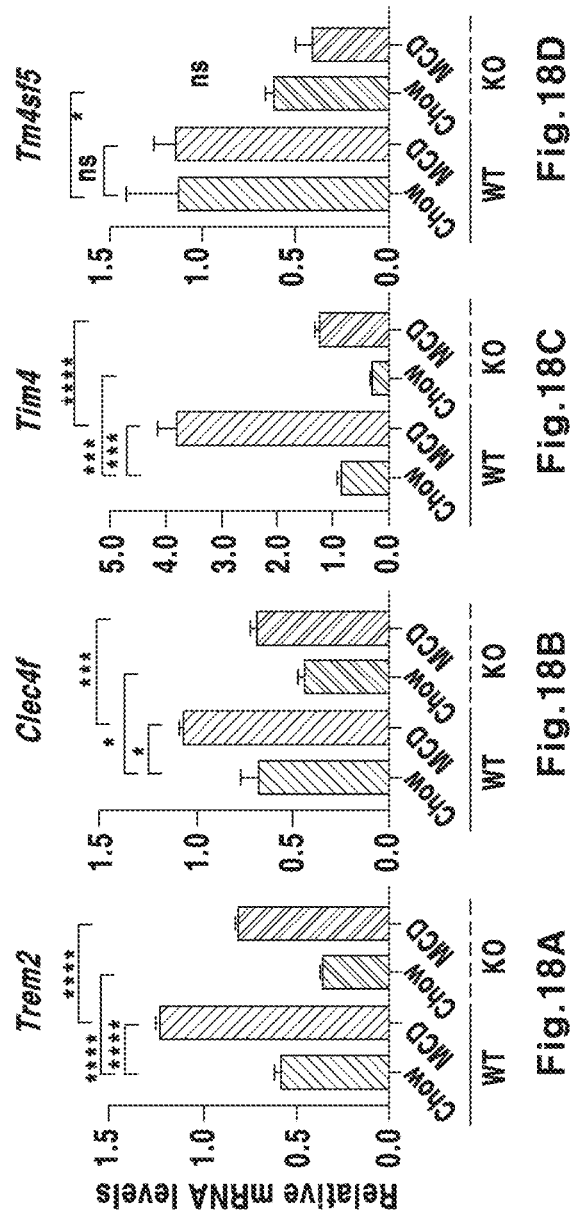

Ccl20

Cxcl10

SEQUENCE LISTING

```
<160> NUMBER OF SEQ ID NOS: 102

<210> SEQ ID NO 1
<211> LENGTH: 20
<212> TYPE: DNA
<213> ORGANISM: Artificial Sequence
<220> FEATURE:
<223> OTHER INFORMATION: TM4SF5 primer (F)

<400> SEQUENCE: 1
cttgctcaac cgcactctat                                              20

<210> SEQ ID NO 2
<211> LENGTH: 22
<212> TYPE: DNA
<213> ORGANISM: Artificial Sequence
<220> FEATURE:
<223> OTHER INFORMATION: TM4SF5 primer (R)

<400> SEQUENCE: 2
atcccacaca gtactatctc ca                                           22

<210> SEQ ID NO 3
<211> LENGTH: 21
<212> TYPE: DNA
<213> ORGANISM: Artificial Sequence
<220> FEATURE:
<223> OTHER INFORMATION: MRC-1 primer (F)

<400> SEQUENCE: 3
gcggaaccac tactgactat g                                            21

<210> SEQ ID NO 4
<211> LENGTH: 20
<212> TYPE: DNA
<213> ORGANISM: Artificial Sequence
<220> FEATURE:
<223> OTHER INFORMATION: MRC-1 primer (R)

<400> SEQUENCE: 4
ctggtcagcg ggtctttatt                                              20

<210> SEQ ID NO 5
<211> LENGTH: 22
<212> TYPE: DNA
<213> ORGANISM: Artificial Sequence
<220> FEATURE:
<223> OTHER INFORMATION: FN1 primer (F)

<400> SEQUENCE: 5
ccacagtgga gtatgtggtt ag                                           22

<210> SEQ ID NO 6
<211> LENGTH: 21
<212> TYPE: DNA
<213> ORGANISM: Artificial Sequence
<220> FEATURE:
<223> OTHER INFORMATION: FN1 primer (R)

<400> SEQUENCE: 6
```
cagtccttta gggcgatcaa t                                              21

<210> SEQ ID NO 7
<211> LENGTH: 21
<212> TYPE: DNA
<213> ORGANISM: Artificial Sequence
<220> FEATURE:
<223> OTHER INFORMATION: TNF alpha primer (F)

<400> SEQUENCE: 7
ccagggacct ctctctaatc a                                              21

<210> SEQ ID NO 8
<211> LENGTH: 20
<212> TYPE: DNA
<213> ORGANISM: Artificial Sequence
<220> FEATURE:
<223> OTHER INFORMATION: TNF alpha primer (R)

<400> SEQUENCE: 8
tcagcttgag ggtttgctac                                                20

<210> SEQ ID NO 9
<211> LENGTH: 20
<212> TYPE: DNA
<213> ORGANISM: Artificial Sequence
<220> FEATURE:
<223> OTHER INFORMATION: IL-1beta primer (F)

<400> SEQUENCE: 9
caaaggcggc caggatataa                                                20

<210> SEQ ID NO 10
<211> LENGTH: 23
<212> TYPE: DNA
<213> ORGANISM: Artificial Sequence
<220> FEATURE:
<223> OTHER INFORMATION: IL-1beta primer (R)

<400> SEQUENCE: 10
ctagggattg agtccacatt cag                                            23

<210> SEQ ID NO 11
<211> LENGTH: 24
<212> TYPE: DNA
<213> ORGANISM: Artificial Sequence
<220> FEATURE:
<223> OTHER INFORMATION: IL-6 primer (F)

<400> SEQUENCE: 11
ccaggagaag attccaaaga tgta                                           24

<210> SEQ ID NO 12
<211> LENGTH: 21
<212> TYPE: DNA
<213> ORGANISM: Artificial Sequence
<220> FEATURE:
<223> OTHER INFORMATION: IL-6 primer (R)

<400> SEQUENCE: 12
cgtcgaggat gtaccgaatt t                                              21

<210> SEQ ID NO 13
<211> LENGTH: 21
<212> TYPE: DNA

```
<213> ORGANISM: Artificial Sequence
<220> FEATURE:
<223> OTHER INFORMATION: CCL2 primer (F)

<400> SEQUENCE: 13
tcatagcagc caccttcatt c                                              21

<210> SEQ ID NO 14
<211> LENGTH: 24
<212> TYPE: DNA
<213> ORGANISM: Artificial Sequence
<220> FEATURE:
<223> OTHER INFORMATION: CCL2 primer (R)

<400> SEQUENCE: 14
ctctgcactg agatcttcct attg                                           24

<210> SEQ ID NO 15
<211> LENGTH: 18
<212> TYPE: DNA
<213> ORGANISM: Artificial Sequence
<220> FEATURE:
<223> OTHER INFORMATION: CCL20 primer (F)

<400> SEQUENCE: 15
tcctggctgc tttgatgt                                                  18

<210> SEQ ID NO 16
<211> LENGTH: 22
<212> TYPE: DNA
<213> ORGANISM: Artificial Sequence
<220> FEATURE:
<223> OTHER INFORMATION: CCL20 primer (R)

<400> SEQUENCE: 16
tttactgagg agacgcacaa ta                                             22

<210> SEQ ID NO 17
<211> LENGTH: 23
<212> TYPE: DNA
<213> ORGANISM: Artificial Sequence
<220> FEATURE:
<223> OTHER INFORMATION: CXCL10 primer (F)

<400> SEQUENCE: 17
ccattctgat ttgctgcctt atc                                            23

<210> SEQ ID NO 18
<211> LENGTH: 22
<212> TYPE: DNA
<213> ORGANISM: Artificial Sequence
<220> FEATURE:
<223> OTHER INFORMATION: CXCL10 primer (R)

<400> SEQUENCE: 18
cctttccttg ctaactgctt tc                                             22

<210> SEQ ID NO 19
<211> LENGTH: 20
<212> TYPE: DNA
<213> ORGANISM: Artificial Sequence
<220> FEATURE:
<223> OTHER INFORMATION: COL1 alpha 1 primer (F)

<400> SEQUENCE: 19
cagactggca acctcaagaa                                                20
```

<210> SEQ ID NO 20
<211> LENGTH: 20
<212> TYPE: DNA
<213> ORGANISM: Artificial Sequence
<220> FEATURE:
<223> OTHER INFORMATION: COL1 alpha 1 primer (R)

<400> SEQUENCE: 20
cagtgacgct gtaggtgaag                                               20

<210> SEQ ID NO 21
<211> LENGTH: 21
<212> TYPE: DNA
<213> ORGANISM: Artificial Sequence
<220> FEATURE:
<223> OTHER INFORMATION: F4/80 primer (F)

<400> SEQUENCE: 21
accacaatac ctacatgcac c                                             21

<210> SEQ ID NO 22
<211> LENGTH: 21
<212> TYPE: DNA
<213> ORGANISM: Artificial Sequence
<220> FEATURE:
<223> OTHER INFORMATION: F4/80 primer (R)

<400> SEQUENCE: 22
aagcaggcga ggaaaagata g                                             21

<210> SEQ ID NO 23
<211> LENGTH: 31
<212> TYPE: DNA
<213> ORGANISM: Artificial Sequence
<220> FEATURE:
<223> OTHER INFORMATION: TNF alpha primer (F)

<400> SEQUENCE: 23
gagtgacaag cctgtagccc atgttgtagc a                                  31

<210> SEQ ID NO 24
<211> LENGTH: 31
<212> TYPE: DNA
<213> ORGANISM: Artificial Sequence
<220> FEATURE:
<223> OTHER INFORMATION: TNF alpha primer (R)

<400> SEQUENCE: 24
gcaatgatcc caaagtagac ctgcccagac t                                  31

<210> SEQ ID NO 25
<211> LENGTH: 22
<212> TYPE: DNA
<213> ORGANISM: Artificial Sequence
<220> FEATURE:
<223> OTHER INFORMATION: KEAP1 primer (F)

<400> SEQUENCE: 25
cacaacagtg tggagaggta tg                                            22

<210> SEQ ID NO 26
<211> LENGTH: 21
<212> TYPE: DNA
<213> ORGANISM: Artificial Sequence
<220> FEATURE:

```
<223> OTHER INFORMATION: KEAP1 primer (R)

<400> SEQUENCE: 26
cggcataaag gagacgattg a                                          21

<210> SEQ ID NO 27
<211> LENGTH: 20
<212> TYPE: DNA
<213> ORGANISM: Artificial Sequence
<220> FEATURE:
<223> OTHER INFORMATION: NRF2 primer (F)

<400> SEQUENCE: 27
gttgcccaca ttcccaaatc                                            20

<210> SEQ ID NO 28
<211> LENGTH: 20
<212> TYPE: DNA
<213> ORGANISM: Artificial Sequence
<220> FEATURE:
<223> OTHER INFORMATION: NRF2 primer (R)

<400> SEQUENCE: 28
cgtagccgaa gaaacctcat                                            20

<210> SEQ ID NO 29
<211> LENGTH: 20
<212> TYPE: DNA
<213> ORGANISM: Artificial Sequence
<220> FEATURE:
<223> OTHER INFORMATION: LDLR primer (F)

<400> SEQUENCE: 29
ctcccgccaa gatcaagaaa                                            20

<210> SEQ ID NO 30
<211> LENGTH: 22
<212> TYPE: DNA
<213> ORGANISM: Artificial Sequence
<220> FEATURE:
<223> OTHER INFORMATION: LDLR primer (R)

<400> SEQUENCE: 30
gtttggagtc aacccagtag ag                                         22

<210> SEQ ID NO 31
<211> LENGTH: 21
<212> TYPE: DNA
<213> ORGANISM: Artificial Sequence
<220> FEATURE:
<223> OTHER INFORMATION: CCL5 primer (F)

<400> SEQUENCE: 31
tgcccacatc aaggagtatt t                                          21

<210> SEQ ID NO 32
<211> LENGTH: 21
<212> TYPE: DNA
<213> ORGANISM: Artificial Sequence
<220> FEATURE:
<223> OTHER INFORMATION: CCL5 primer (R)

<400> SEQUENCE: 32
gatgtactcc cgaacccatt t                                          21
```

```
<210> SEQ ID NO 33
<211> LENGTH: 20
<212> TYPE: DNA
<213> ORGANISM: Artificial Sequence
<220> FEATURE:
<223> OTHER INFORMATION: CXCL1 primer (F)

<400> SEQUENCE: 33
actcaagaat gggcggaaag                                              20

<210> SEQ ID NO 34
<211> LENGTH: 21
<212> TYPE: DNA
<213> ORGANISM: Artificial Sequence
<220> FEATURE:
<223> OTHER INFORMATION: CXCL1 primer (R)

<400> SEQUENCE: 34
cccttctggt cagttggatt t                                            21

<210> SEQ ID NO 35
<211> LENGTH: 22
<212> TYPE: DNA
<213> ORGANISM: Artificial Sequence
<220> FEATURE:
<223> OTHER INFORMATION: CXCL3 primer (F)

<400> SEQUENCE: 35
tcacctcaag aacatccaaa gt                                           22

<210> SEQ ID NO 36
<211> LENGTH: 22
<212> TYPE: DNA
<213> ORGANISM: Artificial Sequence
<220> FEATURE:
<223> OTHER INFORMATION: CXCL3 primer (R)

<400> SEQUENCE: 36
agacaagctt tcttcccatt ct                                           22

<210> SEQ ID NO 37
<211> LENGTH: 22
<212> TYPE: DNA
<213> ORGANISM: Artificial Sequence
<220> FEATURE:
<223> OTHER INFORMATION: CXCL5 primer (F)

<400> SEQUENCE: 37
caatcttcgc tcctccaatc tc                                           22

<210> SEQ ID NO 38
<211> LENGTH: 20
<212> TYPE: DNA
<213> ORGANISM: Artificial Sequence
<220> FEATURE:
<223> OTHER INFORMATION: CXCL5 primer (R)

<400> SEQUENCE: 38
aggaggctca tagtggtcaa                                              20

<210> SEQ ID NO 39
<211> LENGTH: 19
<212> TYPE: DNA
<213> ORGANISM: Artificial Sequence
<220> FEATURE:
<223> OTHER INFORMATION: CXCL6 primer (F)
```

<400> SEQUENCE: 39
ccctggaccc agtaagaag                                            19

<210> SEQ ID NO 40
<211> LENGTH: 22
<212> TYPE: DNA
<213> ORGANISM: Artificial Sequence
<220> FEATURE:
<223> OTHER INFORMATION: CXCL6 primer (R)

<400> SEQUENCE: 40
taaacttcag ggagaagcgt ag                                        22

<210> SEQ ID NO 41
<211> LENGTH: 20
<212> TYPE: DNA
<213> ORGANISM: Artificial Sequence
<220> FEATURE:
<223> OTHER INFORMATION: CXCL8 primer (F)

<400> SEQUENCE: 41
cttggcagcc ttcctgattt                                           20

<210> SEQ ID NO 42
<211> LENGTH: 22
<212> TYPE: DNA
<213> ORGANISM: Artificial Sequence
<220> FEATURE:
<223> OTHER INFORMATION: CXCL8 primer (R)

<400> SEQUENCE: 42
gggtggaaag gtttggagta tg                                        22

<210> SEQ ID NO 43
<211> LENGTH: 26
<212> TYPE: DNA
<213> ORGANISM: Artificial Sequence
<220> FEATURE:
<223> OTHER INFORMATION: CXCL10 primer (F)

<400> SEQUENCE: 43
gtaataactc taccctggca ctataa                                    26

<210> SEQ ID NO 44
<211> LENGTH: 22
<212> TYPE: DNA
<213> ORGANISM: Artificial Sequence
<220> FEATURE:
<223> OTHER INFORMATION: CXCL10 primer (R)

<400> SEQUENCE: 44
gatgggaaag gtgagggaaa ta                                        22

<210> SEQ ID NO 45
<211> LENGTH: 19
<212> TYPE: DNA
<213> ORGANISM: Artificial Sequence
<220> FEATURE:
<223> OTHER INFORMATION: Tm4sf5 primer (F)

<400> SEQUENCE: 45
gtcttctcct ccgcctttg                                            19

<210> SEQ ID NO 46
<211> LENGTH: 23

<212> TYPE: DNA
<213> ORGANISM: Artificial Sequence
<220> FEATURE:
<223> OTHER INFORMATION: Tm4sf5 primer (R)

<400> SEQUENCE: 46
ggtagtccca cttgttgtct att                                         23

<210> SEQ ID NO 47
<211> LENGTH: 21
<212> TYPE: DNA
<213> ORGANISM: Artificial Sequence
<220> FEATURE:
<223> OTHER INFORMATION: Tnf alpha primer (F)

<400> SEQUENCE: 47
ttgtctactc ccaggttctc t                                           21

<210> SEQ ID NO 48
<211> LENGTH: 23
<212> TYPE: DNA
<213> ORGANISM: Artificial Sequence
<220> FEATURE:
<223> OTHER INFORMATION: Tnf alpha primer (R)

<400> SEQUENCE: 48
gaggttgact ttctcctggt atg                                         23

<210> SEQ ID NO 49
<211> LENGTH: 20
<212> TYPE: DNA
<213> ORGANISM: Artificial Sequence
<220> FEATURE:
<223> OTHER INFORMATION: Il-6 primer (F)

<400> SEQUENCE: 49
cttccatcca gttgccttct                                             20

<210> SEQ ID NO 50
<211> LENGTH: 22
<212> TYPE: DNA
<213> ORGANISM: Artificial Sequence
<220> FEATURE:
<223> OTHER INFORMATION: Il-6 primer (R)

<400> SEQUENCE: 50
ccttctgtga ctccagctta tc                                          22

<210> SEQ ID NO 51
<211> LENGTH: 25
<212> TYPE: DNA
<213> ORGANISM: Artificial Sequence
<220> FEATURE:
<223> OTHER INFORMATION: Ccl2 primer (F)

<400> SEQUENCE: 51
gatcctcagg accatactgg ataag                                       25

<210> SEQ ID NO 52
<211> LENGTH: 23
<212> TYPE: DNA
<213> ORGANISM: Artificial Sequence
<220> FEATURE:
<223> OTHER INFORMATION: Ccl2 primer (R)

<400> SEQUENCE: 52

```
gaaggttcaa ggatgaaggt ttg                                            23

<210> SEQ ID NO 53
<211> LENGTH: 22
<212> TYPE: DNA
<213> ORGANISM: Artificial Sequence
<220> FEATURE:
<223> OTHER INFORMATION: Arg-1 primer (F)

<400> SEQUENCE: 53
gtccctaatg acagctcctt tc                                             22

<210> SEQ ID NO 54
<211> LENGTH: 22
<212> TYPE: DNA
<213> ORGANISM: Artificial Sequence
<220> FEATURE:
<223> OTHER INFORMATION: Arg-1 primer (R)

<400> SEQUENCE: 54
ccacactgac tcttccattc tt                                             22

<210> SEQ ID NO 55
<211> LENGTH: 21
<212> TYPE: DNA
<213> ORGANISM: Artificial Sequence
<220> FEATURE:
<223> OTHER INFORMATION: Ym-1 primer (F)

<400> SEQUENCE: 55
gctaaggaca ggccaataga a                                              21

<210> SEQ ID NO 56
<211> LENGTH: 20
<212> TYPE: DNA
<213> ORGANISM: Artificial Sequence
<220> FEATURE:
<223> OTHER INFORMATION: Ym-1 primer (R)

<400> SEQUENCE: 56
gcattccagc aaaggcatag                                                20

<210> SEQ ID NO 57
<211> LENGTH: 21
<212> TYPE: DNA
<213> ORGANISM: Artificial Sequence
<220> FEATURE:
<223> OTHER INFORMATION: Mrc-1 primer (F)

<400> SEQUENCE: 57
cagctggtcc tttgtttgaa a                                              21

<210> SEQ ID NO 58
<211> LENGTH: 21
<212> TYPE: DNA
<213> ORGANISM: Artificial Sequence
<220> FEATURE:
<223> OTHER INFORMATION: Mrc-1 primer (R)

<400> SEQUENCE: 58
ggcgagcatc aagagtaaag a                                              21

<210> SEQ ID NO 59
<211> LENGTH: 24
<212> TYPE: DNA
<213> ORGANISM: Artificial Sequence
```

```
<220> FEATURE:
<223> OTHER INFORMATION: F4/80 primer (F)

<400> SEQUENCE: 59
cgtcaggtac gggatgaata taag                                          24

<210> SEQ ID NO 60
<211> LENGTH: 22
<212> TYPE: DNA
<213> ORGANISM: Artificial Sequence
<220> FEATURE:
<223> OTHER INFORMATION: F4/80 primer (R)

<400> SEQUENCE: 60
atcttggaag tggatggcat ag                                            22

<210> SEQ ID NO 61
<211> LENGTH: 21
<212> TYPE: DNA
<213> ORGANISM: Artificial Sequence
<220> FEATURE:
<223> OTHER INFORMATION: alpha Sma  primer (F)

<400> SEQUENCE: 61
gtcccagaca tcagggagta a                                             21

<210> SEQ ID NO 62
<211> LENGTH: 21
<212> TYPE: DNA
<213> ORGANISM: Artificial Sequence
<220> FEATURE:
<223> OTHER INFORMATION: alpha Sma  primer (R)

<400> SEQUENCE: 62
tcggatactt cagcgtcagg a                                             21

<210> SEQ ID NO 63
<211> LENGTH: 20
<212> TYPE: DNA
<213> ORGANISM: Artificial Sequence
<220> FEATURE:
<223> OTHER INFORMATION: Col1 alpha 1  primer (F)

<400> SEQUENCE: 63
agacctgtgt gttccctact                                               20

<210> SEQ ID NO 64
<211> LENGTH: 21
<212> TYPE: DNA
<213> ORGANISM: Artificial Sequence
<220> FEATURE:
<223> OTHER INFORMATION: Col1 alpha 1  primer (R)

<400> SEQUENCE: 64
gaatccatcg gtcatgctct c                                             21

<210> SEQ ID NO 65
<211> LENGTH: 22
<212> TYPE: DNA
<213> ORGANISM: Artificial Sequence
<220> FEATURE:
<223> OTHER INFORMATION: Lamc2 primer (F)

<400> SEQUENCE: 65
ctccgtggta caaggtctta tg                                            22
```

<210> SEQ ID NO 66
<211> LENGTH: 22
<212> TYPE: DNA
<213> ORGANISM: Artificial Sequence
<220> FEATURE:
<223> OTHER INFORMATION: Lamc2 primer (R)

<400> SEQUENCE: 66
actccctatc tcctgctcta tc                                              22

<210> SEQ ID NO 67
<211> LENGTH: 20
<212> TYPE: DNA
<213> ORGANISM: Artificial Sequence
<220> FEATURE:
<223> OTHER INFORMATION: Nos2 primer (F)

<400> SEQUENCE: 67
agcctgtgag acctttgatg                                                 20

<210> SEQ ID NO 68
<211> LENGTH: 22
<212> TYPE: DNA
<213> ORGANISM: Artificial Sequence
<220> FEATURE:
<223> OTHER INFORMATION: Nos2 primer (R)

<400> SEQUENCE: 68
cctcttgtct ttgacccagt ag                                              22

<210> SEQ ID NO 69
<211> LENGTH: 22
<212> TYPE: DNA
<213> ORGANISM: Artificial Sequence
<220> FEATURE:
<223> OTHER INFORMATION: Ppar gamma primer (F)

<400> SEQUENCE: 69
ctggcctccc tgatgaataa ag                                              22

<210> SEQ ID NO 70
<211> LENGTH: 22
<212> TYPE: DNA
<213> ORGANISM: Artificial Sequence
<220> FEATURE:
<223> OTHER INFORMATION: Ppar gamma primer (R)

<400> SEQUENCE: 70
aggctccata aagtcaccaa ag                                              22

<210> SEQ ID NO 71
<211> LENGTH: 20
<212> TYPE: DNA
<213> ORGANISM: Artificial Sequence
<220> FEATURE:
<223> OTHER INFORMATION: Ccl20 primer (F)

<400> SEQUENCE: 71
tctgctcttc cttgctttgg                                                 20

<210> SEQ ID NO 72
<211> LENGTH: 20
<212> TYPE: DNA
<213> ORGANISM: Artificial Sequence
<220> FEATURE:
<223> OTHER INFORMATION: Ccl20 primer (R)

```
<400> SEQUENCE: 72
cccagttctg ctttggatca                                             20

<210> SEQ ID NO 73
<211> LENGTH: 19
<212> TYPE: DNA
<213> ORGANISM: Artificial Sequence
<220> FEATURE:
<223> OTHER INFORMATION: Cxcl10 primer (F)

<400> SEQUENCE: 73
tttctgcctc atcctgctg                                              19

<210> SEQ ID NO 74
<211> LENGTH: 23
<212> TYPE: DNA
<213> ORGANISM: Artificial Sequence
<220> FEATURE:
<223> OTHER INFORMATION: Cxcl10 primer (R)

<400> SEQUENCE: 74
cagacatctc tgctcatcat tct                                         23

<210> SEQ ID NO 75
<211> LENGTH: 22
<212> TYPE: DNA
<213> ORGANISM: Artificial Sequence
<220> FEATURE:
<223> OTHER INFORMATION: beta-actin primer (F)

<400> SEQUENCE: 75
gtgacgttga catccgtaaa ga                                          22

<210> SEQ ID NO 76
<211> LENGTH: 19
<212> TYPE: DNA
<213> ORGANISM: Artificial Sequence
<220> FEATURE:
<223> OTHER INFORMATION: beta-actin primer (R)

<400> SEQUENCE: 76
gccggactca tcgtactcc                                              19

<210> SEQ ID NO 77
<211> LENGTH: 22
<212> TYPE: DNA
<213> ORGANISM: Artificial Sequence
<220> FEATURE:
<223> OTHER INFORMATION: Trem2 primer (F)

<400> SEQUENCE: 77
caccatcact ctgaagaacc tc                                          22

<210> SEQ ID NO 78
<211> LENGTH: 20
<212> TYPE: DNA
<213> ORGANISM: Artificial Sequence
<220> FEATURE:
<223> OTHER INFORMATION: Trem2 primer (R)

<400> SEQUENCE: 78
gcacctccac cagtactttc                                             20

<210> SEQ ID NO 79
```

```
<211> LENGTH: 23
<212> TYPE: DNA
<213> ORGANISM: Artificial Sequence
<220> FEATURE:
<223> OTHER INFORMATION: Clec4f primer (F)

<400> SEQUENCE: 79
ctatccagag gcttagggac tat                                              23

<210> SEQ ID NO 80
<211> LENGTH: 20
<212> TYPE: DNA
<213> ORGANISM: Artificial Sequence
<220> FEATURE:
<223> OTHER INFORMATION: Clec4f primer (R)

<400> SEQUENCE: 80
gcaactgcac cagagaacta                                                  20

<210> SEQ ID NO 81
<211> LENGTH: 22
<212> TYPE: DNA
<213> ORGANISM: Artificial Sequence
<220> FEATURE:
<223> OTHER INFORMATION: Tim4 primer (F)

<400> SEQUENCE: 81
gctgcctcag aggatacaat aa                                               22

<210> SEQ ID NO 82
<211> LENGTH: 22
<212> TYPE: DNA
<213> ORGANISM: Artificial Sequence
<220> FEATURE:
<223> OTHER INFORMATION: Tim4 primer (R)

<400> SEQUENCE: 82
ggaattggga catgaacctt tg                                               22

<210> SEQ ID NO 83
<211> LENGTH: 21
<212> TYPE: DNA
<213> ORGANISM: Artificial Sequence
<220> FEATURE:
<223> OTHER INFORMATION: Gapdh primer (F)

<400> SEQUENCE: 83
gtggcaaagt ggagattgtt g                                                21

<210> SEQ ID NO 84
<211> LENGTH: 20
<212> TYPE: DNA
<213> ORGANISM: Artificial Sequence
<220> FEATURE:
<223> OTHER INFORMATION: Gapdh primer (R)

<400> SEQUENCE: 84
cgttgaattt gccgtgagtg                                                  20

<210> SEQ ID NO 85
<211> LENGTH: 21
<212> TYPE: DNA
<213> ORGANISM: Artificial Sequence
<220> FEATURE:
<223> OTHER INFORMATION: Cd206 primer (F)

<400> SEQUENCE: 85
```
ggcgagcatc aagagtaaag a                                              21

<210> SEQ ID NO 86
<211> LENGTH: 21
<212> TYPE: DNA
<213> ORGANISM: Artificial Sequence
<220> FEATURE:
<223> OTHER INFORMATION: Cd206 primer (R)

<400> SEQUENCE: 86
cataggtcag tcccaaccaa a                                              21

<210> SEQ ID NO 87
<211> LENGTH: 62
<212> TYPE: RNA
<213> ORGANISM: Artificial Sequence
<220> FEATURE:
<223> OTHER INFORMATION: Human Tm4sf5, #2  (sense)

<400> SEQUENCE: 87
ccggaccatg tgtacgggaa aatgtgcctc gaggcacatt ttcccgtaca catggttttt    60
tg                                                                   62

<210> SEQ ID NO 88
<211> LENGTH: 62
<212> TYPE: RNA
<213> ORGANISM: Artificial Sequence
<220> FEATURE:
<223> OTHER INFORMATION: Human Tm4sf5, #2  (anit-sense)

<400> SEQUENCE: 88
aattcaaaaa accatgtgta cgggaaaatg tgcctcgagg cacattttcc cgtacacatg    60
gt                                                                   62

<210> SEQ ID NO 89
<211> LENGTH: 54
<212> TYPE: RNA
<213> ORGANISM: Artificial Sequence
<220> FEATURE:
<223> OTHER INFORMATION: Human Tm4sf5, #4  (sense)

<400> SEQUENCE: 89
ccggccatct cagcttgcaa gtcctcgagg acttgcaagc tgagatggtt tttg          54

<210> SEQ ID NO 90
<211> LENGTH: 54
<212> TYPE: RNA
<213> ORGANISM: Artificial Sequence
<220> FEATURE:
<223> OTHER INFORMATION: Human Tm4sf5, #4  (anti-sense)

<400> SEQUENCE: 90
aattcaaaaa ccatctcagc ttgcaagtcc tcgaggactt gcaagctgag atgg          54

<210> SEQ ID NO 91
<211> LENGTH: 21
<212> TYPE: DNA
<213> ORGANISM: Artificial Sequence
<220> FEATURE:
<223> OTHER INFORMATION: CMV Forward Primer

<400> SEQUENCE: 91
cgctattacc atggtgatgc g                                              21

```
<210> SEQ ID NO 92
<211> LENGTH: 21
<212> TYPE: DNA
<213> ORGANISM: Artificial Sequence
<220> FEATURE:
<223> OTHER INFORMATION: TM4SF5 Reverse Primer

<400> SEQUENCE: 92
agacaccgag aggcagtaga t                                              21

<210> SEQ ID NO 93
<211> LENGTH: 23
<212> TYPE: RNA
<213> ORGANISM: Artificial Sequence
<220> FEATURE:
<223> OTHER INFORMATION: sgRNA1 targeting Tm4sf5 Exon 1

<400> SEQUENCE: 93
gaggttgccg tccgtccagg tgg                                            23

<210> SEQ ID NO 94
<211> LENGTH: 23
<212> TYPE: RNA
<213> ORGANISM: Artificial Sequence
<220> FEATURE:
<223> OTHER INFORMATION: sgRNA2 targeting Tm4sf5 Exon 1

<400> SEQUENCE: 94
gctgaggttg ccgtccgtcc agg                                            23

<210> SEQ ID NO 95
<211> LENGTH: 23
<212> TYPE: RNA
<213> ORGANISM: Artificial Sequence
<220> FEATURE:
<223> OTHER INFORMATION: RG1 targeting Tm4sf5 Exon 3

<400> SEQUENCE: 95
gcgggagctg ggctccgaat tgg                                            23

<210> SEQ ID NO 96
<211> LENGTH: 23
<212> TYPE: RNA
<213> ORGANISM: Artificial Sequence
<220> FEATURE:
<223> OTHER INFORMATION: RG2 targeting Tm4sf5 Exon 3

<400> SEQUENCE: 96
ttaagcattt gggtccaatt cgg                                            23

<210> SEQ ID NO 97
<211> LENGTH: 23
<212> TYPE: RNA
<213> ORGANISM: Artificial Sequence
<220> FEATURE:
<223> OTHER INFORMATION: RG3 targeting Tm4sf5 Exon 3

<400> SEQUENCE: 97
tgagaaatcc tgtttgatct tgg                                            23

<210> SEQ ID NO 98
<211> LENGTH: 23
<212> TYPE: RNA
<213> ORGANISM: Artificial Sequence
<220> FEATURE:
<223> OTHER INFORMATION: RG4 targeting Tm4sf5 Exon 3
```

```
<400> SEQUENCE: 98
aggtattagg ggtggcctat ggg                                               23

<210> SEQ ID NO 99
<211> LENGTH: 16
<212> TYPE: DNA
<213> ORGANISM: Artificial Sequence
<220> FEATURE:
<223> OTHER INFORMATION: Mouse TM4SF5 primer (Forward)

<400> SEQUENCE: 99
tatgcgggag gcactg                                                       16

<210> SEQ ID NO 100
<211> LENGTH: 20
<212> TYPE: DNA
<213> ORGANISM: Artificial Sequence
<220> FEATURE:
<223> OTHER INFORMATION: Mouse TM4SF5 primer (Reverse)

<400> SEQUENCE: 100
gggtgaccac tcagacttcc                                                   20

<210> SEQ ID NO 101
<211> LENGTH: 21
<212> TYPE: RNA
<213> ORGANISM: Artificial Sequence
<220> FEATURE:
<223> OTHER INFORMATION: Ccl20 siRNA (sense)

<400> SEQUENCE: 101
ggaggaaaug aucacagcut t                                                 21

<210> SEQ ID NO 102
<211> LENGTH: 21
<212> TYPE: RNA
<213> ORGANISM: Artificial Sequence
<220> FEATURE:
<223> OTHER INFORMATION: Ccl20 siRNA (anti-sense)

<400> SEQUENCE: 102
agcugugauc auuuccucct t                                                 21
```

IMMUNOSUPPRESSANT COMPRISING TSAHC OR A PHARMACEUTICALLY ACCEPTABLE SALTS THEREOF AS AN ACTIVE INGREDIENT

CROSS-REFERENCE TO RELATED APPLICATIONS

This application claims priority to Korean Application No. 10-2020-0148087, filed Nov. 6, 2020, the entirety of which is incorporated herein by reference.

REFERENCE TO SEQUENCE LISTING SUBMITTED ON COMPUTER

The content of the ASCII text file of the sequence listing named "18931-32_2022-02-09_CorrectedSequenceListing" filed concurrently herewith is 21,020 bytes in size with a created date of Jan. 21, 2022, and is being electronically submitted via EFS-Web, is incorporated herein by reference in its entirety.

BACKGROUND OF THE INVENTION

1. Field of the Invention

The present invention relates to an immunosuppressant comprising TSAHC or a pharmaceutically acceptable salt thereof as an active ingredient.

2. Description of the Related Art

The liver performs many functions in our body, such as metabolism of lipids, detoxification, bile excretion, storage of various nutrients, hematopoiesis, blood coagulation, and regulation of circulating blood volume. Therefore, when hepatic impairment occurs, various functions are reduced, and in the worst case, it becomes difficult to maintain life.

The functions of the liver are specifically as follows. First, since the liver has a function of managing energy metabolism, all nutrients such as carbohydrates, fats, and proteins including amino acids absorbed from food are metabolized into substances capable of producing energy in the liver and supplied or stored throughout the body. Second, about 2,000 enzymes, albumin, and coagulation factors present in the liver synthesize, store, and distribute serum proteins, bile acid, phospholipids, and fats such as cholesterol. Third, the liver has detoxification and decomposition functions. Since the liver detoxifies drugs, alcohol, and toxic substances, liver cells are easily damaged in this process. Since the liver detoxifies drugs, alcohol, and toxic substances, liver cells are easily damaged in this process. Therefore, liver disease caused by drugs, poisons or alcohol can be occurred frequently. In addition, the liver has a function of excreting various metabolites to the duodenum, an immune function, and the like, so it is important for maintaining life.

Liver disease can be classified into viral liver disease, alcoholic liver disease, drug toxic liver disease, fatty liver, autoimmune liver disease, metabolic liver disease and others depending on the cause. Liver disease is the leading cause of death not only in Korea but also in the world because liver disease has no early symptoms and is only discovered after a fairly advanced stage. Therefore, there is a need for research on a method for effectively diagnosing liver disease and a method for treating the same. On the other hand, when liver resection is attempted or liver transplantation is performed due to liver disease, an excessive inflammatory reaction in the liver tissue can be a problem, and therefore immunosuppressant measures are required.

Inflammation in the human liver is the cause and characteristic of several chronic liver diseases. Alcohol, viral infection, toxin accumulation, and chronic damage of liver epithelial cells due to abnormal metabolic function and accompanying inflammatory response due to cell death play an important role in inducing and exacerbating additional liver disease. In the course of the onset and exacerbation of the liver disease, an excessive inflammatory reaction also acts as the etiology. However, when liver resection and liver transplantation are attempted as a means of treatment according to the worsening of the liver disease, the need for immunosuppression arises because an excessive inflammatory reaction may cause a problem.

Nonalcoholic fatty liver caused by abnormality in metabolic function in normal liver is accompanied by inflammation due to cell damage and death, and worsens into steatohepatitis, further exacerbating into fibrosis and liver cirrhosis resulting in the accumulation of extracellular matrix and abnormal proliferation of cells. In addition, carcinogenesis of fibrotic/hardened liver tissue can be suppressed or promoted depending on the metabolic-inflammatory environment changes and interactions due to the interaction between epithelial cells and immune cells including macrophages, T cells and NK (natural killer) cells present in the liver.

Transmembrane 4 L six family member 5 (TM4SF5) is tetraspanin that passes through the cell membrane 4 times, and it was confirmed that the expression of TM4SF5 was increased in hepato-epithelial cells and macrophages due to the action of various cytokines and chemokines following chronic hepato-epithelial cell damage. Therefore, the interaction of hepatic epithelial cells and macrophages depends on the expression of TM4SF5 to remodel the inflammatory response and immune environment of the liver, leading to liver fibrosis or cirrhosis beyond steatohepatitis. Ultimately, at the time of cancer formation, TM4SF5 expression in epithelial cells enables the process of immune escape that can suppress the anticancer activity of immune cells including NK (natural killer) cells, so that it can effectively increase carcinogenesis and cancer incidence.

Therefore, if a small molecule compound or antibody is used as an inhibitor to suppress the expression of TM4SF5 or to regulate the function of TM4SF5, it is expected to be able to inhibit and control the interaction between hepatic epithelial cells and immune cells in liver tissue, thereby suppressing and controlling the aggravation of steatohepatitis and fibrosis/sclerosis.

As prior literatures related to TM4SF, there are Korean Patent No. 10-2112760, which discloses that fatty liver and steatohepatitis are induced when TM4SF5 is overexpressed, and Korean Patent No. 10-1368871, which discloses a kit for diagnosing liver fibrosis, cirrhosis, or alcoholic liver damage comprising an antibody against TM4SF5 protein. However, it has not been disclosed that TM4SF5 acts as an immunosuppressant by regulating the interaction between hepatic epithelial cells and immune cells.

Meanwhile, 4'-(p-toluenesulfonylamido)-4-hydroxychalcone, also called TSAHC, is a chalcone-based compound and can be prepared through synthesis. As prior literatures related to TSAHC, there are Korean Patent No. 10-0751899, which discloses a use for preventing and treating diabetes, obesity, cancer and viral diseases caused by 4'-(p-toluenesulfonylamido)-4-hydroxychalcone glycosidase and Korean Patent No. 10-0934706, which discloses an anticancer use of 4'-(p-toluenesulfonylamido)-4-hydroxychalcone. However, there is no disclosure regarding the use of TSAHC for inhibiting immune activity in relation to macrophages.

Accordingly, the present inventors have studied with the expectation that if a small molecule compound or antibody is used as an inhibitor to suppress the expression of TM4SF5 or to regulate the function of TM4SF5, the aggravation of steatohepatitis and fibrosis/sclerosis can be suppressed and controlled by regulating the interaction between hepatic epithelial cells and immune cells in liver tissue and by inhibiting immune response.

During the study, the present inventors confirmed that the expression of TM4SF5, a membrane protein, was induced by cytokines or chemokines (CCL2, CCL5, CCL20, CXCL10, etc.), which induced intercellular interaction, and leads to reorganization of inflammatory environment according to the activation of macrophages, abnormalities in metabolic function, and induction of diseases such as liver fibrosis and liver cirrhosis. In addition, the present inventors confirmed that the expression and secretion of cytokines/chemokines such as IL6, IL1β, TNFα, CXCL1, CXCL6, CCL2, CCL5, CCL20 and CXCL10 according to the expression of the TM4SF5 gene and protein were inhibited by the treatment of TSAHC. The present inventors also confirmed that cytokines (IL6, IL1β and TNFα) and chemokines (CCL2, CCL5, CCL20, CXCL1, CXCL2, CXCL3, CXCL6, CXCL8, CXCL10 and CCR10) mediated by the expression of TM4SF5 induced inflammatory responses of liver tissues, hepatic epithelial cells and macrophages, and abnormalities in metabolic function and correlated with liver tissue damage, recruitment and activation of immune cells in genetically modified animals, leading to the completion of the present invention.

SUMMARY OF THE INVENTION

It is an object of the present invention to provide an immunosuppressive method by administering an effective amount of 4'-(p-toluenesulfonylamido)-4-hydroxychalcone to a subject.

To achieve the above object, the present invention provides an immunosuppressant comprising 4'-(p-toluenesulfonylamido)-4-hydroxychalcone or a pharmaceutically acceptable salt thereof as an active ingredient.

Advantageous Effect

The present invention relates to an immunosuppressant comprising TSAHC or a pharmaceutically acceptable salt thereof as an active ingredient. TSAHC treatment suppressed the expression and secretion of cytokines/chemokines such as IL6, IL1β, TNFα, CXCL1, CXCL2, CXCL3, CXCL6, CXCL8, CCL2, CCL5, CCL20, CXCL10 and CCR10 according to the expression of TM4SF5 gene and protein, and the cytokines or chemokines mediated by the expression of TM4SF5 induced abnormalities in the inflammatory response and metabolic function of liver tissues, hepatic epithelial cells and macrophages, and correlated with liver tissue damage and immune cell recruit in TM4SF5 transgenic animals. Therefore, a composition comprising TSAHC or a pharmaceutically acceptable salt thereof as an active ingredient can be effectively used as an immunosuppressant.

BRIEF DESCRIPTION OF THE DRAWINGS

FIG. 4 is a set of graphs showing the results of confirming the CCL20 (A) and CXCL10 (B) mRNA expressions according to the treatment of IL-6 and TSAHC in Hep3B cell line expressing TM4SF5.

FIG. 5 is a set of photographs showing the results of confirming the degree of liver damage, inflammation, and fibrosis according to the Ccl20 expression suppression and $CCl_4$ treatment.

FIG. 11 is a set of graphs showing the results of confirming the changes of CCL2 (A), TNF-α (B), IL-6 (C) and IL-1β (D) mRNA expressions according to the treatment of TSAHC.

FIG. 13 is a set of graphs showing the results of confirming the mRNA levels of the M1 macrophage markers Ccl2 (A), Tnfa (B) and Il-6 (C) or the M2 macrophage marker Arg1 (D) in macrophages differentiated from BMDM cells using a methionine-choline deficient mouse model.

FIG. 18 is a set of graphs showing the results of confirming the mRNA expression levels of Trem2 (A), Clec4f (B), Tim4 (C) and Tm4sf5 (D), the markers indicating the presence and activity of Kupffer macrophages according to the Tm4sf5 gene expression using a methionine-choline deficient mouse model.

DESCRIPTION OF THE PREFERRED EMBODIMENTS

Figure 1A:
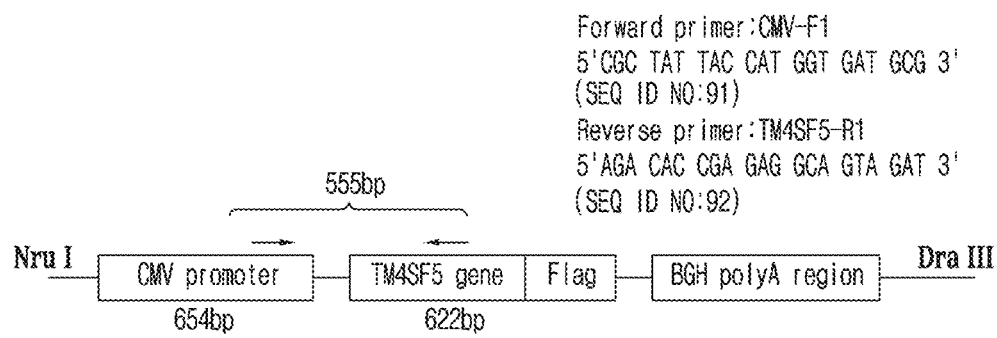
FIGS. 1A and 1B are diagrams showing the results of preparing mice in which human TM4SF5 gene is overexpressed in all organs.

Hereinafter, the present invention is described in detail.

The present invention provides an immunosuppressant comprising 4'-(p-toluenesulfonylamido)-4-hydroxychalcone or a pharmaceutically acceptable salt thereof as an active ingredient.

The term used in this specification, "4'-(p-toluenesulfonylamido)-4-hydroxychalcone" is a chalcone-based compound, which can be prepared by synthesis. The 4'-(p-toluenesulfonylamido)-4-hydroxychalcone can be used as TSAHC and is a compound having the following properties:

Melting point: 106~107° C., 1H NMR (300 MHz; MeOD) d 225 (3H, s), 682 (2H, d, J=86 Hz), 723 (4H, m), 742 (1H, d, J=155 Hz), 751 (2H, d, J=86 Hz), 766 (1H, d, J=155 Hz), 773 (2H, d, J=83 Hz), 790 (2H, dd, J1=87, J2=20 Hz) and HERIMS m/z 3931035 [M+] (calcd for C22H19NO4S, 3931034).

The 4'-(p-toluenesulfonylamido)-4-hydroxychalcone has the structure of Formula 1 below.

[Formula 1]

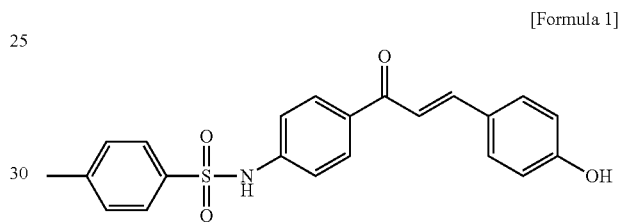

The term used in this specification, "TM4SF5 (transmembrane 4 L6 family member 5) protein" refers to a protein included in tetraspanin, tetraspan or TM4SF (transmembrane 4 super family), which is a membrane receptor group that passes through a cell membrane 4 times, and has a structure similar to each other that passes through a cell membrane 4 times. The TM4SF5 protein shares a structure including four hydrophobic sites that are biochemically presumed to be transmembrane domains.

The 4'-(p-toluenesulfonylamido)-4-hydroxychalcone or a pharmaceutically acceptable salt thereof can inhibit the secretion of inflammatory cytokine or chemokine in liver epithelial cells or macrophages.

The cytokine or chemokine is dependent on the expression of TM4SF5 in liver tissues, hepatic epithelial cells or macrophages.

The cytokine or chemokine can regulate the increase of the TM4SF5 or SIRT1 expression in epithelial cells or the increase of the phosphorylation of STAT3 Tyrosine 705.

The cytokine or chemokine can regulate the recruit of immune cells to liver tissues or the increase of the phosphorylation of STAT3 Tyrosine 705 in hepatic epithelial cells, or regulate the expression of collagen I alpha 1 or laminin γ2.

The cytokine or chemokine can increase the expression of TM4SF5 by interacting with macrophages.

The cytokine or chemokine can be at least one selected from the group consisting of CXCL1, CXCL6, CCL20, CXCL2, CXCL8, CXCL3, CXCL5, IL1β, CCL2, CCL5, CCR10 and CXCL10.

The cytokine or chemokine can be CCL2, CCL5, CCL20 or CXCL10.

The 4'-(p-toluenesulfonylamido)-4-hydroxychalcone or a pharmaceutically acceptable salt thereof can decrease the secretion of at least one selected from the group consisting of IL-6, CCL2, IL1β and TNFα in macrophages.

The 4'-(p-toluenesulfonylamido)-4-hydroxychalcone or a pharmaceutically acceptable salt thereof can inhibit the binding of TM4SF5 to IL6Rα in hepatic epithelial cells.

The 4'-(p-toluenesulfonylamido)-4-hydroxychalcone or a pharmaceutically acceptable salt thereof can inhibit the activation of M1-type macrophages by inhibiting the binding of TM4SF5 to GLUT1 in macrophages, the sensitivity of glycolysis (or ECAR; Extra Cellular Acidification Rate) to extracellular glucose, or glycolysis.

The 4'-(p-toluenesulfonylamido)-4-hydroxychalcone or a pharmaceutically acceptable salt thereof can inhibit the increase in oxygen consumption due to the conversion of M1-type macrophages to M2 type or mitochondrial respiration by continuous treatment of CCL20 or CXCL10 cytokine or chemokine or exposure thereto.

The 4'-(p-toluenesulfonylamido)-4-hydroxychalcone or a pharmaceutically acceptable salt thereof can suppress the chronic activation of M2-type macrophages by suppressing the expressions of Mannose receptor C-type 1 (MRC1, CD206), fibronectin (FN1), arginase I (Arg1), and peroxisome proliferator-activated receptor gamma (Pparγ) in macrophages by continuous treatment of cytokine or chemokine or exposure thereto.

The immunosuppressant is useful for the prevention or treatment of autoimmune disease, excessive inflammatory action due to tissue resection, or transplant rejection of an organ or tissue.

The organ or tissue can be liver or liver tissue.

The immunosuppressant of the present invention can include a pharmaceutically acceptable carrier.

The pharmaceutically acceptable carrier included in the immunosuppressant of the present invention is the one that is generally used for the preparation of a pharmaceutical formulation, which is exemplified by lactose, dextrose, sucrose, sorbitol, mannitol, starch, acacia rubber, calcium phosphate, alginate, gelatin, calcium silcate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The immunosuppressant of the present invention can additionally include lubricants, wetting agents, sweeteners, flavors, emulsifiers, suspending agents, and preservatives, in addition to the above ingredients.

The immunosuppressant of the present invention can be administered orally or parenterally. The parenteral administration herein can be performed by intravenous injection, subcutaneous injection, intradermal injection, sublingual injection, buccal mucosal injection, intramuscular injection, enema injection, etc.

A suitable dosage of the immunosuppressant of the present invention varies depending on factors such as formulation method, administration method, age, weight, gender, pathological condition, food, administration time, administration route, excretion rate and reaction sensitivity of a patient. An effective dosage for the desired treatment or prophylaxis can be easily determined and prescribed by an ordinary skilled doctor. According to a preferred embodiment of the present invention, the daily dose of the pharmaceutical composition of the present invention is 0.001-100 mg/kg.

The immunosuppressant of the present invention can be formulated by the method that can be performed by those in the art by using a pharmaceutically acceptable carrier and/or excipient in the form of unit dose or in multi-dose container. The formulation can be in the form of solution, suspension or emulsion in oil or water-soluble medium, extract, powder, granule, tablet or capsule. At this time, a dispersing agent or a stabilizer can be additionally included.

Figure 2:
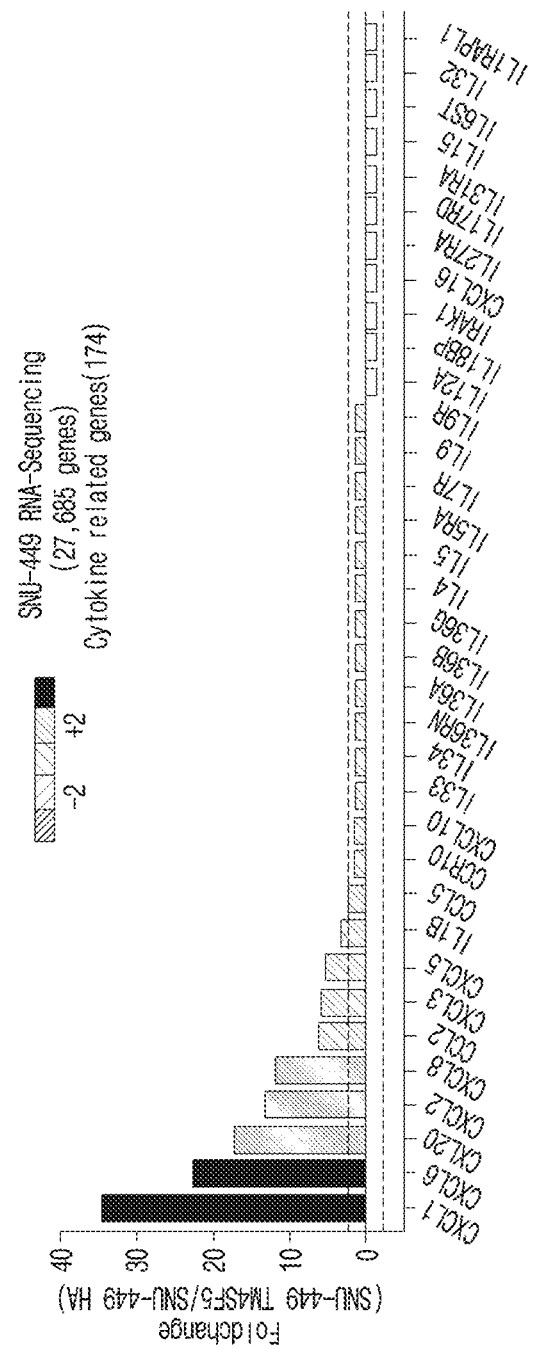
FIG. 2 is a diagram showing the mRNA expression levels of CXCL1, CXCL6, CCL20, CXCL2, CXCL8, CXCL3, CXCL5, IL1β, CCL2, CCL5, CCR10, CXCL10, etc. in cells expressing TM4SF5 compared to hepatic epithelial cells not expressing TM4SF5.

In a preferred embodiment of the present invention, it was confirmed that the mRNA expressions of CXCL1, CXCL6, CCL20, CXCL2, CXCL8, CXCL3, CXCL5, IL1β, CCL2, CCL5, CCR10, CXCL10, etc. were increased in cells expressing TM4SF5 compared to hepatic epithelial cells not expressing TM4SF5 (see FIG. 2). In addition, it was confirmed that the phosphorylation of sub-signaling factors by TM4SF5 such as FAK, c-Src and STAT3 was increased concurrently when TM4SF5 was expressed (see FIG. 3). As a result of confirming whether the mRNA expression of CCL20 and CXCL10 was suppressed by the treatment of TSAHC in Hep3B cell line treated with IL-6, it was also confirmed that the mRNA expression level of CCL20 and CXCL10 increased by IL-6 was decreased by the treatment of TSAHC (see FIGS. 4A and 4B). In addition, it was confirmed that the degree of inflammation and fibrosis of the liver induced by the treatment of $CCl_4$ was remarkably suppressed according to the inhibition of the Ccl20 expression (see FIG. 5). It was also confirmed that the mRNA levels of Col1α1, Ccl20, F4/80 and α-Sma were increased by the treatment of $CCl_4$, but the expression was decreased when the expression of Ccl20 was suppressed during the $CCl_4$ treatment (see FIGS. 6A to 6D). In order to confirm the interaction between hepatic epithelial cells and macrophages by the expression of TM4SF5, the binding of TM4SF5 and Glut1 was confirmed. As a result, it was confirmed that WT TM4SF5 was bound to WT Glut1 (see FIG. 7). As a result of measuring the activation of glycolytic function according to the treatment of TSAHC, it was confirmed that the cells expressing TM4SF5 showed higher glycolytic function than that of the (EV) cell line not expressing TM4SF5 even under the various glucose adding conditions, and this was not changed by the control compound (4'-methoxy-4-dihydroxychalcone) treatment, but decreased by the treatment of TSAHC (see FIG. 8). In addition, it was confirmed that the glycolytic function was much higher in M0 THP-1 cells expressing TM4SF5 than that in M0 THP-1 not expressing TM4SF5, and that the glycolytic function in M0 THP-1 cells expressing TM4SF5 was higher than that in the vehicle-treated control group due to the additional CCL20 or CXCL10 treatment (see FIGS. 9A to 9D). It was also confirmed that TM4SF5 was bound to IL6-Ra, and this binding was inhibited by the treatment of TSAHC (see FIG. 10). As a result of confirming the mRNA expression changes of CCL20, TNF-α, IL-6 and IL-1β according to the treatment of TSAHC, the expression of each mRNA was higher in the cell line expressing TM4SF5 than in the cell line not expressing TM4SF5, and the expression was decreased by the treatment of TSAHC (see FIGS. 11A to 11D). When M1 type macrophages were treated with CCL20 or CXCL10, respectively or together, the mRNA levels of M1 type macrophage markers were decreased compared to the control group. On the other hand, when M2 type macrophages were treated with CCL20 alone or together with CXCL10, the mRNA levels of M2 type macrophage markers were statistically significantly increased (see FIGS. 12A and 12B). It was also confirmed that the mRNA expression of the markers showing activity as M1 type macrophages was increased in macrophages differentiated from BMDM cells of normal mice using mice fed a normal diet or a methionine-choline deficient diet. On the other hand, the mRNA expression of the markers showing activity as M2 type macrophages was increased in Tm4sf5 gene-deficient mice (see FIGS. 13A to 13D). When Tm4sf5 gene was expressed in a methionine-choline deficient mouse model, symptoms of steatohepatitis accompanied by liver fibrosis were induced. On the other hand, such phenomena occurred insignificantly in the liver tissue of KO mice (see FIG. 14). When Tm4sf5 gene was expressed in a methionine-choline deficient mouse model, the expression levels of F4/80, Ccl20, and Cxcl10 were increased in the liver tissue, fat was excessively accumulated, and immune cells were concentrated. On the other hand, such phenomena occurred insignificantly in the liver tissue of KO mice (see FIGS. 15 and 16). In addition, when Tm4sf5 gene was expressed in a high-fat diet mouse model, macrophages were excessively concentrated. On the other hand, such phenomena occurred insignificantly in the liver tissue of KO mice (see FIGS. 17A and 17B). When Tm4sf5 gene was expressed in methionine-choline deficient mice, the mRNA expression levels of the markers indicating the presence and activity of Kupffer macrophages were increased. On the other hand, such phenomena occurred insignificantly in the liver tissue of KO mice (see FIGS. 18A and 18B). It was also confirmed that the Tm4sf5 mRNA expression level, ALT level, and liver tissue weight and body weight were increased in a mouse model that could be accompanied by cell damage and inflammation when liver fibrosis was induced by the treatment of $CCl_4$, and the corresponding levels were decreased according to the treatment of TSAHC (see FIGS. 19A to 19C). The level of liver damage was also reduced according to the treatment of TSAHC (see FIG. 20). It was confirmed that the mRNA expression of Ccl20 and Cxcl10 was increased and the corresponding mRNA expression was decreased in the mouse model according to the treatment of TSAHC (see FIGS. 21A to 21D). It was also confirmed that immunostaining for F4/80, a macrophage marker, was prominent in the mouse model. It was also confirmed that the F4/80 mRNA expression was reduced in the mouse model according to the treatment of TSAHC (see FIGS. 22A and 22B). It was confirmed that immunostaining for α-SMA was prominent in the mouse model, and that the α-SMA mRNA expression was reduced according to the treatment of TSAHC (see FIGS. 23A and 23B). It was also confirmed that the degree of liver damage and the recruit of immune cells were reduced when the expression of Col1a1 or Lamc2 was suppressed in the mouse model (see FIG. 24). The phosphorylation of STAT3 tyrosine 705 increased by the treatment of $CCL_4$ was decreased by the suppression of the laminin γ2 and collagen 1 alpha1 expression (see FIG. 25). In addition, when TM4SF5 was expressed, the expression of chemokines such as NRF2, CCL2, CCL5, CCL20, CXCL1, CXCL6, CXCL8 and CXCL10 was increased, but this expression was decreased by the expression of KEAP1 (Kelch Like ECH Associated Protein 1) (see FIG. 26).

Hereinafter, the present invention will be described in detail by the following examples. However, the following examples are only for illustrating the present invention, and the contents of the present invention are not limited thereto.

Example 1: Cell Culture

AML12, a normal mouse cell line, cell lines prepared by infecting SNU449 not expressing TM4SF5 among human liver cancer cell lines with a retrovirus expressing TM4SF5 (SNU449Tp and SNU449T$_7$), a SNU449Cp cell line infected with a control virus, cell lines expressing TM4SF5 endogenously (Hep3B, HepG2, and Huh7), human embryonic kidney cell line (HEK293 and HEK293T, KCLB, Korea, HEK293FT, Thermo, USA) were cultured in DMEM or RPMI-1640 (WelGene, Daegu, Korea) supplemented with 10% FBS and antibiotics (Invitrogen, CA, USA) in a 37° C., 5% $CO_2$ incubator. Primary hepatocytes and bone marrow-derived macrophage (BMDM) were isolated from C57BL/6 normal WT or Tm4sf5$^{-/-}$ KO mice and cultured in DMEM (Dulbecco's Modified Eagle's medium) or RPMI (Roswell Park Memorial Institute Medium, Hyclone) supplemented with 10% FBS (GenDEPOT), 1% penicillin/streptomycin (GenDEPOT), and 1×GlutaMax (Invitrogen, USA) in the same manner as above. THP-1 cells, human monocytes, were cultured in RPMI-1640 (Hyclone) supplemented with 10% FBS (GenDEPOT), 1% penicillin/streptomycin (GenDEPOT), and 0.1% β-mercaptoethanol.

Example 2: Gene Injection (Transfection or Infection) and Expression Inhibition

An empty vector (EV) or the cDNA contained in a mammalian expression plasmid was transfected into a cell line using lipofectamine 3000 (Thermo Fisher Scientific Inc.) or lentivirus obtained by infecting a host cell with the empty vector or a lentivirus vector containing the cDNA was infected to a cell line to artificially express the gene in the cell line to be studied. Meanwhile, siRNA and pLKO.1-shRNA (control sequence or sequence targeting a specific sequence of a target gene) were transfected into the cell line using Lipofectamine RNAiMAX Transfection Reagent (Thermo Fisher Scientific Inc.) for 48 hours or infected to lentivirus.

Example 3: Inhibition and Induction of TM4SF5 Expression

To suppress the expression of TM4SF5 in hepatic epithelial cells, pLKO.1-shRNA (control sequence or TM4SF5 sequence #2 or #4) was transfected into the cell line for 48 hours or infected to lentivirus. An expression vector in which genes for multiple tags are linked to human TM4SF5 gene was prepared (Cell Metabolism 2019, Vol 29: 1306-1319). The expression vector was transfected into the cell line or infected to retrovirus or lentivirus. In order to express TM4SF5 in THP-1 cells, the cells were infected with empty pLJM1 vector (control, purchased from Addgene), pLJM1-TM4SF5 lentivirus, pBabe-HAII or pBabe-HAII-TM4SF5 retrovirus.

Sense or anti-sense shRNA sequence for suppressing TM4SF5 gene expression (5'→3')

Human Tm4sf5, #2
Sense:
(SEQ. ID. NO: 87)
CCGGACCATGTGTACGGGAAAATGTGCCTCGAGGCACATTTTCCCGTA

CACATGGTTTTTG

Anti-sense:
(SEQ. ID. NO: 88)
AATTCAAAAAACCATGTGTACGGGAAAATGTGCCTCGAGGCACATTTT

CCCGTACACATGGT

Human Tm4sf5, #4
Sense:
(SEQ. ID. NO: 89)
CCGGCCATCTCAGCTTGCAAGTCCTCGAGGACTTGCAAGCTGAGATGG

TTTTTG

Anti-sense:
(SEQ. ID. NO: 90)
AATTCAAAAACCATCTCAGCTTGCAAGTCCTCGAGGACTTGCAAGCTG

AGATGG

Example 4: Construction of a Mouse in which Human TM4SF5 Gene is Overexpressed in all Organs (pcDNA3-FLAG-hTM4SF5-Transgenic Mouse: Tg$^{TM4SF5}$)

Figure 1B:
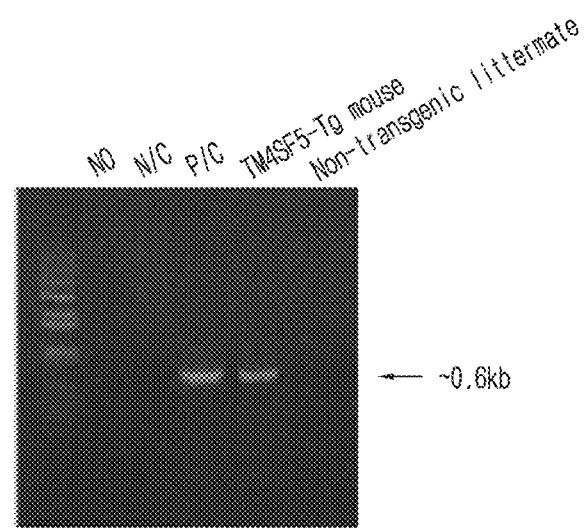

As shown in FIG. 1, the entire pcDNA3-Flag-hTM4SF5 sequence including human TM4SF5 gene (NM_003963) and the BGH (bovine growth hormone) poly(A) region were purified and microinjected into C57BL/6 mouse fertilized eggs. After confirming the 2-week-old founder mouse by PCR with primers [CMV Forward-CGCTATTACCATGGT-GATGCG (SEQ. ID. NO: 91), TM4SF5 Reverse-AGACACCGAGAGGCAGTAGAT (SEQ. ID. NO: 92)], overexpressed mice were prepared. FVB/N Tg$^{TM4SF5}$ mice were obtained by 10-generation breeding C57BL/6 Tg$^{TM4SF5}$ mice with FVB/N mice.

Example 5: Construction of TM4SF5 Gene Knockout (KO) Mouse

C57BL/6 mice were used to construct cas9/RGEN KO mice. Mice with several bp deletions (29, 240, 502, 510, 522, and 538 bp) were obtained using RGEN sites [sgRNA sequences for mouse Tm4sf5 Exon 1 target(5'-3'): sgRNA1 GAGGTTGCCGTCCGTCCAGGTGG (SEQ. ID. NO: 93), sgRNA2 GCTGAGGTTGCCGTCCGTCCAGG (SEQ. ID. NO: 94); Sequence for Tm4sf5 Exon 3 Target: RG1-GCGG-GAGCTGGGCTCCGAATTGG (SEQ. ID. NO: 95), RG2-TTAAGCATTTGGGTCCAATTCGG (SEQ. ID. NO: 96), RG3-TGAGAAATCCTGTTTGATCTTGG (SEQ. ID. NO: 97), and RG4-AGGTATTAGGGGTGGCCTATGGG(SEQ. ID. NO: 98)]. Mutant mice were found by observing the heteroduplex formation between WT/mutant PCR products through T7E1 assay using mouse TM4SF5 primers (Forward-GTAGTATGCGGGAGGCACTG (SEQ. ID. NO: 99), Reverse-GGGTGACCACTCAGACTTCC(SEQ. ID. NO: 100), and the precisely knocked-out mice were used for the experiment. The experiment was performed with the mice in which 29 bps including Exon 1 having the 36$^{th}$ threonine where extracellular loop 2 of mouse TM4SF5 begins are deleted (Tm4sf5 Exon1$^{-/-}$) or the mice in which 522 bps including Exon 3 from the nucleotide sequence having the 112$^{th}$ leucine are deleted (Tm4sf5 Exon3$^{-/-}$).

Example 6: Isolation of Hepatic Epithelial Cells and Bone Marrow-Derived Macrophages (BMDM) from Mice Hepatocytes were isolated using 4-week-old BALB/C, 52-78-week-old C57BL/6, or indicated week-old C57BL/6 mice. First, the perfusate was passed through the liver to drain blood, and then hepatocytes were isolated using collagen type II. The separated hepatocytes were filtered with a 40 μm cell filter, and then centrifuged to obtain the cells that settled to the bottom. The obtained hepatocytes were cultured in William's E medium (1% penicillin/streptomycin, 10% FBS), and at this time, the cells were cultured on a plate pre-coated with collagen.

Bone marrow-derived macrophages (BMDM) were obtained by crushing the femur and tibia of the mouse, and centrifuging the solution containing the cells filtered through 100 μm nylon mesh at a gradient of 37.5% percoll. Erythrocytes were lysed with RBS lysis solution. The cells were cultured in DMEM supplemented with 10% FBS, 1% penicillin/streptomycin (GenDEPOT) and recombinant mouse M-CSF (20 ng/ml; R&D systems) for 4 days. On the 4$^{th}$ day, BMDM cells were activated to M1 or M2 type by treating the cells with LPS and murine INF-γ (100 nM and 20 ng/ml; Invivogen and BioLegend) or mouse IL-4 and IL-13 (20 ng/ml; BioLegend).

Example 7: Suppression of Expression Through Injection of siRNA of Genes Dependent on TM4SF5 Expression in Liver Inflammation and Fibrosis Model Induced by CCl$_4$ Treatment SiCOL1A1 (Thermo Scientifics, catalog number: AM16708, siRNA ID 145490) and siLAMC2 (Thermo Scientifics, catalog number: AM16708, siRNA ID 100303) were diluted in PBS and administered to the tail vein of BALB/C mice twice a week at a concentration of 3 mg/kg, respectively, for 3 weeks. At the same time, CCl$_4$ (5 mg/kg in 40% olive oil) was also intraperitoneally administered to the mice twice a week for 3 weeks. After 3 weeks, the animal was dissected to obtain liver tissue, and the protein and mRNA expression levels were analyzed by immunohistochemistry, Western blotting and PCR using the liver tissue.

12-week-old normal WT or Tm4sf5$^{-/-}$ KO mice (5 per group) were intraperitoneally injected with CCl$_4$ (TRC, Canada, C176905, 10 mg/kg/40% olive oil) twice a week for 4 weeks. Ccl20 siRNA [sense 5'-GGAGGAAAUGAU-CACAGCUtt-3' (SEQ. ID. NO: 101), antisense 5'-AGCU-GUGAUCAUUUCCUCCtt-3 (SEQ. ID. NO: 102) was purchased from Ambion (Austin Texas, USA) and diluted to an appropriate concentration in PBS. Ccl20 siRNA (1.66 mg/kg) or vehicle was intravenously injected into the mice twice a week. After 4 weeks, liver and blood samples of the animals were obtained.

Experimental Example 1: Confirmation of Suppression of Expression and Secretion of Inflammatory Cytokines and Chemokines in TM4SF5 Expression-Dependent Hepatic Epithelial Cells by TSAHC Treatment <1-1> Confirmation of Inflammatory Cytokine and Chemokine mRNA Expression To confirm whether the TSAHC treatment affects the expression and secretion of inflammatory cytokines and chemokines in TM4SF5 expression-dependent hepatic epithelial cells, RNA-Seq analysis and mRNA-Seq analysis comparing the mRNA expression were performed in SNU449-HA cell line in which the control vector was safely injected into SNU449, SNU449-TM4SF5-HA cell line injected with TM4SF5 expression vector, and SNU449-TM4SF5-HA cell line treated with 10 μM of TSAHC for 24 hours using the liver tissue of Tg$^{TM4SF5}$ overexpressing TM4SF5 or Tm4sf5$^{-/-}$ KO C57BL/6 mice in Macrogen, Inc. (Seoul, Korea).

The experimental procedure for mRNA-Seq analysis included the followings. First, total RNA was isolated from TSAHC-treated or untreated cells and tissues expressing or not expressing TM4SF5. DNA contamination was eliminated by treating with DNAse. Using 1 μg of RNA and Truseq RNA sample prep Kit v2, a cDNA library was constructed including polyA-selected RNA extraction, RNA fragmentation, non-specific hexamer primed reverse transcription, and 100 nucleotide paired-end sequencing with illumina HiSeq4000. RNA library was constructed through qPCR using an agilent technologies 2100 bioanalyzer according to qPCR quantification protocol guide. Quality control analysis of the raw reads obtained through sequencing was performed. Pre-treatment processing was performed to remove artifacts such as low quality product or adapter sequence, contaminant DNA, and PCR duplicates. Aligned reads were generated after mapping the pre-treated reads to reference genome using HISAT2 program considering splice. Transcript assembly was performed through the String Tie program using paired information of the aligned reads based on the reference. The expression level obtained through the transcript quantification of each sample was calculated as a normalization value considering the transcript length and depth of coverage. Expression profile was extracted by performing within normalization with FPKM (Fragment Per Kilobase of transcript per Million mapped reads) value or RPKM (Reads Per Kilobase of transcript per Million mapped reads) value. Genes or transcripts differentially expressed were selected by statistical hypothesis testing with the expression values of two or more groups under the conditions that did not express or express TM4SF5 or treated with TSAHC. For the differentially expressed genes, functional annotation and gene-set enrichment analysis based on GO and KEGG databases were performed.

As a result, as shown in FIG. 2, it was confirmed that the mRNA expression of CXCL1, CXCL6, CCL20, CXCL2, CXCL8, CXCL3, CXCL5, IL1β, CCL2, CCL5, CCR10, CXCL10, etc. was increased in the cells expressing TM4SF5 compared to the hepatic epithelial cells not expressing TM4SF5.

<1-2> Confirmation of Inflammatory Cytokine and Chemokine Protein Expression

Western blotting was performed with the extracts of the cell lines in which the expression of TM4SF5 was regulated by transforming SNU449, which does not natively express TM4SF5, with empty vector (EV) or TM4SF5 expression vector or the cell lines in which the expression of TM4SF5 was regulated by transforming Huh7, HepG2, and Hep3B liver epithelial cells, which natively express TM4SF5, with control shRNA or shTM4SF5 using antibodies against the indicated proteins.

Specifically, the obtained cell extract was centrifuged at 4° C., 13000×g for 30 minutes, and only the supernatant was transferred to a new microcentrifuge tube. After quantification using BCA reagent (Thermo Scientifics), 4× sample buffer [100% glycerol 4 ml, Tris-HCl, pH 6.8, 2.4 ml, SDS 0.8 g, bromophenol blue 4 mg, beta-mercaptoethanol 0.4 ml, $H_2O$ 3.1 ml (per 10 ml)] was added to the tube, and then boiled at 100° C. for 5 minutes. After performing SDS-PAGE electrophoresis with the above sample, the protein was transferred to a Nitrocellulose Membranes Protran™ nitrocellulose membrane (Whatman), and then pretreated with 5% skim milk for 1 hour. After the pretreatment, the membrane was reacted with the primary antibodies of $pY^{705}STAT3$ (Millipore, USA), CXCL10 and CCL20 (Santa Cruz, USA) at 4° C. for 15 hours. On the next day, the membrane was reacted with a secondary antibody and developed on an X-ray film using ECL (Pierce, USA).

Figure 3:
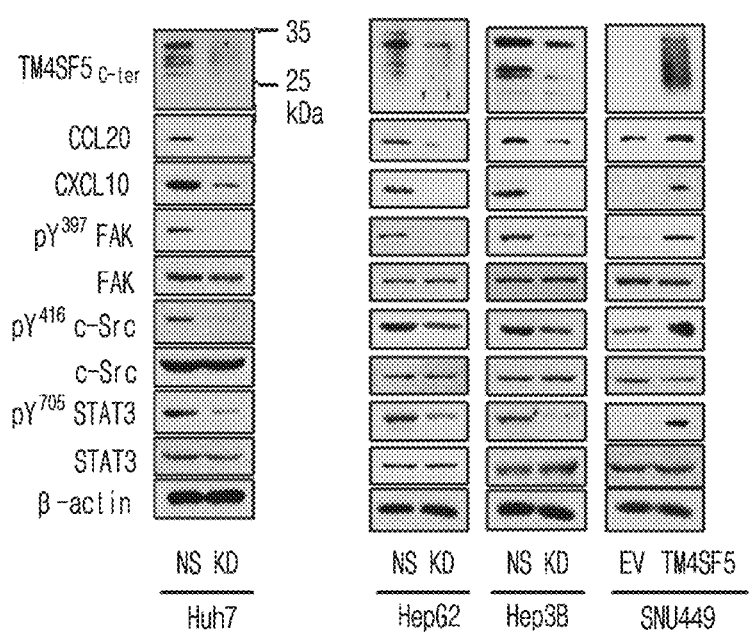
FIG. 3 is a set of photographs showing the protein levels of CCL20 and CXCL10 and the phosphorylation levels of FAK, c-Src, and STAT3 in cells expressing TM4SF5 compared to hepatic epithelial cells not expressing TM4SF5.
Figure 6A:
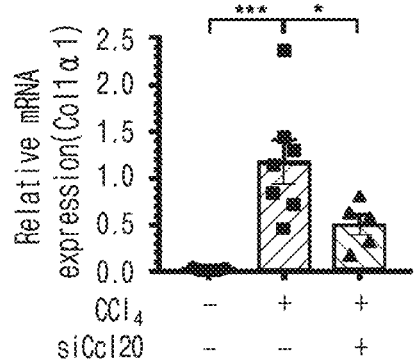
FIG. 6 is a set of graphs showing the results of confirming the expression levels of Col1α1 (A), F4/80 (C), Ccl20 (B) and a-Sma (D) mRNA according to the Ccl20 expression suppression and $CCl_4$ treatment.
Figure 6B:
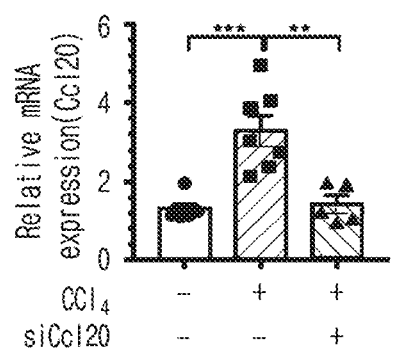
Figure 6C:
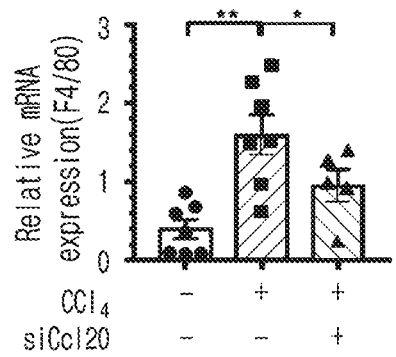
Figure 6D:
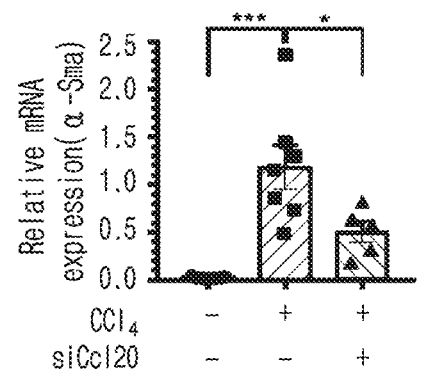

As a result, as shown in FIG. 3, in the case of expressing TM4SF5 compared to the case of not expressing TM4SF5, not only the expression of chemokines such as CCL20 and CXCL10 was increased, but also the phosphorylation of down-stream signaling factors of TM4SF5 such as FAK, c-Src, and STAT3 was also increased.

Experimental Example 2: Confirmation of Suppression of CCL20 and CXCL10 mRNA Expression in IL-6-Treated Hep3B Cell Line According to TSAHC Treatment Hep3B cell line expressing TM4SF5 that was not treated with IL-6 or treated at a concentration of 100 ng/ml was treated with or without TSAHC at a concentration of 0.1 or 0.5 μM for 24 hours. Then, qRT-PCR was performed using the cells.

Specifically, to perform qRT-PCR, the cells or tissues were disrupted using Qiazol (Qiagen, USA), to which chloroform was added, and the upper organic layer was separated by centrifugation at 4° C., 12,000×g for 15 minutes. RNA was precipitated by adding isopropanol to the separated organic layer, followed by washing with 70% ethanol. RNA pellet was isolated by centrifugation at 7,500×g for 5 minutes, ethanol was evaporated for 10 minutes, and dissolved in 30 μl of DEPC-water. After removing gDNA from the dissolved RNA, it was reverse transcribed using a reverse transcription kit (Toyobo, Japan) to obtain cDNA. The expression was measured by real-time PCR (Biorad, USA) with the obtained cDNA using 2×Eva green master mix (Labopass, Korea) and 0.4 μM forward/reverse primers. The expression amount was calculated using the modified delta-delta Ct method of Pfaffl. The sequences of the primers for RT-PCR or qRT-PCR used in the present invention are shown in Table 1.

TABLE 1

| Gene | Forward primer | SEQ. ID. NO | Reverse primer | SEQ. ID. NO |
|---|---|---|---|---|
| Human | | | | |
| TM4SF5 | CTTGCTCAACCGCACTCTAT | 1 | ATCCCACACAGTACTATCTCCA | 2 |
| MRC-1 | GCGGAACCACTACTGACTATG | 3 | CTGGTCAGCGGGTCTTTATT | 4 |
| FN1 | CCACAGTGGAGTATGTGGTTAG | 5 | CAGTCCTTTAGGGCGATCAAT | 6 |
| TNFα | CCAGGGACCTCTCTCTAATCA | 7 | TCAGCTTGAGGGTTTGCTAC | 8 |
| IL-1beta | CAAAGGCGGCCAGGATATAA | 9 | CTAGGGATTGAGTCCACATTCAG | 10 |
| IL-6 | CCAGGAGAAGATTCCAAAGATGTA | 11 | CGTCGAGGATGTACCGAATTT | 12 |

TABLE 1-continued

| Gene | Forward primer | SEQ. ID. NO | Reverse primer | SEQ. ID. NO |
|---|---|---|---|---|
| CCL2 | TCATAGCAGCCACCTTCATTC | 13 | CTCTGCACTGAGATCTTCCTATTG | 14 |
| CCL20 | TCCTGGCTGCTTTGATGT | 15 | TTTACTGAGGAGACGCACAATA | 16 |
| CXCL10 | CCATTCTGATTTGCTGCCTTATC | 17 | CCTTTCCTTGCTAACTGCTTTC | 18 |
| COL1α1 | CAGACTGGCAACCTCAAGAA | 19 | CAGTGACGCTGTAGGTGAAG | 20 |
| F4/80 | ACCACAATACCTACATGCACC | 21 | AAGCAGGCGAGGAAAAGATAG | 22 |
| TNF-α | GAGTGACAAGCCTGTAGCCCATGTTGTAGCA | 23 | GCAATGATCCCAAAGTAGACCTGCCCAGACT | 24 |
| KEAP1 | CACAACAGTGTGGAGAGGTATG | 25 | CGGCATAAAGGAGACGATTGA | 26 |
| NRF2 | GTTGCCCACATTCCCAAATC | 27 | CGTAGCCGAAGAAACCTCAT | 28 |
| LDLR | CTCCCGCCAAGATCAAGAAA | 29 | GTTTGGAGTCAACCCAGTAGAG | 30 |
| CCL5 | TGCCCACATCAAGGAGTATTT | 31 | GATGTACTCCCGAACCCATTT | 32 |
| CXCL1 | ACTCAAGAATGGGCGGAAAG | 33 | CCCTTCTGGTCAGTTGGATTT | 34 |
| CXCL3 | TCACCTCAAGAACATCCAAAGT | 35 | AGACAAGCTTTCTTCCCATTCT | 36 |
| CXCL5 | CAATCTTCGCTCCTCCAATCTC | 37 | AGGAGGCTCATAGTGGTCAA | 38 |
| CXCL6 | CCCTGGACCCAGTAAGAAG | 39 | TAAACTTCAGGGAGAAGCGTAG | 40 |
| CXCL8 | CTTGGCAGCCTTCCTGATTT | 41 | GGGTGGAAAGGTTTGGAGTATG | 42 |
| CXCL10 | GTAATAACTCTACCCTGGCACTATAA | 43 | GATGGGAAAGGTGAGGGAAATA | 44 |
| Mouse | | | | |
| Tm4sf5 | GTCTTCTCCTCCGCCTTTG | 45 | GGTAGTCCCACTTGTTGTCTATT | 46 |
| Tnf-α | TTGTCTACTCCCAGGTTCTCT | 47 | GAGGTTGACTTTCTCCTGGTATG | 48 |
| Il-6 | CTTCCATCCAGTTGCCTTCT | 49 | CCTTCTGTGACTCCAGCTTATC | 50 |
| Ccl2 | GATCCTCAGGACCATACTGGATAAG | 51 | GAAGGTTCAAGGATGAAGGTTTG | 52 |
| Arg-1 | GTCCCTAATGACAGCTCCTTTC | 53 | CCACACTGACTCTTCCATTCTT | 54 |
| Ym-1 | GCTAAGGACAGGCCAATAGAA | 55 | GCATTCCAGCAAAGGCATAG | 56 |
| Mrc-1 | CAGCTGGTCCTTTGTTTGAAA | 57 | GGCGAGCATCAAGAGTAAAGA | 58 |
| F4/80 | CGTCAGGTACGGGATGAATATAAG | 59 | ATCTTGGAAGTGGATGGCATAG | 60 |
| α-Sma | GTCCCAGACATCAGGGAGTAA | 61 | TCGGATACTTCAGCGTCAGGA | 62 |

TABLE 1-continued

| Gene | Forward primer | SEQ. ID. NO | Reverse primer | SEQ. ID. NO |
|---|---|---|---|---|
| Col1α1 | AGACCTGTGTGTTCCCTACT | 63 | GAATCCATCGGTCATGCTCTC | 64 |
| Lamc2 | CTCCGTGGTACAAGGTCTTATG | 65 | ACTCCCTATCTCCTGCTCTATC | 66 |
| Nos2 | AGCCTGTGAGACCTTTGATG | 67 | CCTCTTGTCTTTGACCCAGTAG | 68 |
| Ppar-γ | CTGGCCTCCCTGATGAATAAAG | 69 | AGGCTCCATAAAGTCACCAAAG | 70 |
| Ccl20 | TCTGCTCTTCCTTGCTTTGG | 71 | CCCAGTTCTGCTTTGGATCA | 72 |
| Cxcl10 | TTTCTGCCTCATCCTGCTG | 73 | CAGACATCTCTGCTCATCATTCT | 74 |
| beta-actin | GTGACGTTGACATCCGTAAAGA | 75 | GCCGGACTCATCGTACTCC | 76 |
| Trem2 | CACCATCACTCTGAAGAACCTC | 77 | GCACCTCCACCAGTACTTTC | 88 |
| Clec4f | CTATCCAGAGGCTTAGGGACTAT | 79 | GCAACTGCACCAGAGAACTA | 80 |
| Tim4 | GCTGCCTCAGAGGATACAATAA | 81 | GGAATTGGGACATGAACCTTTG | 82 |
| Gapdh | GTGGCAAAGTGGAGATTGTTG | 83 | CGTTGAATTTGCCGTGAGTG | 84 |
| Cd206 | GGCGAGCATCAAGAGTAAAGA | 85 | CATAGGTCAGTCCCAACCAAA | 86 |

As a result, as shown in FIGS. 4A and 4B, it was confirmed that the mRNA expression levels of CCL20 and CXCL10 increased by IL-6 were reduced by the treatment of TSAHC.

Experimental Example 3: Confirmation of Liver Damage, Inflammation and Fibrosis According to Suppression of Ccl20 Expression by $CCl_4$ Treatment As shown in the scheme of FIG. 5, 12-week-old normal C57BL/6 mice were intraperitoneally injected with $CCl_4$ (40% in olive oil) at a concentration of 10 mg/kg body weight twice a week for 26 days. At the same time, siRNA against CCL20 (Amibon, Austin Texas, USA, Assay ID 72932, sense 5'-GGAGGAAAUGAUCACAGCUtt-3', antisense 5'-AGCUGUGAUCAUUUCCUCCtt-3') dissolved in PBS at a concentration of 1.66 mg/kg was intravenously injected for 26 days before the $CCl_4$ injection. After 26 days of the injection, the mice were sacrificed, and the liver tissue was obtained. Then, the disease state of the liver was investigated by performing immunohistochemistry (IHC), Masson's trichrome staining and qRT-PCR.

Specifically, for H&E staining, the tissue was placed in a 60° C. oven for about 20 minutes to separate the tissue from paraffin, and when the paraffin melted, the tissue was immersed in xylene three times for 5 minutes each. The tissue was put into 100%→90%→80%→70% ethanol→distilled water for 3 minutes each in the order, and then immersed in a hematoxylin solution for 5 minutes to react. After sufficiently washing the tissue with tap water, it was reacted with an eosin solution for about 20 minutes, and washed again with tap water. Then, the tissue was immersed in 70%→80%→90%→100% ethanol→xylene for 3 minutes each in the order for dehydration, followed by mounting on a slide.

Paraffin blocks and liver tissue sections for immunohistochemical staining were obtained from Abion Inc. (Seoul, Korea). As antibodies, F4/80 (Cell Signaling Technology), Ccl20, laminin γ2 (Santa Cruz Biotechnology) were used.

For Masson's trichrome staining, the tissue was first separated from paraffin and then reacted in a preheated bouin's solution for 1 hour. After rinsing the tissue with tap water until the solution was completely drained, it was reacted in a hematoxylin solution for 10 minutes, and then rinsed again with tap water. Then, the tissue was reacted in a biebrich scarlet-acid fuchsin solution for 5 minutes, immersed in distilled water, and reacted in a phosphotungstic/phosphomolybdic acid solution for 15 minutes. The tissue was immersed in an Aniline blue solution for 10 minutes and 1% acetic acid for 1 minute for dehydration. The tissue was immersed in xylene, followed by mounting on a slide.

As a result, as shown in FIG. 5, in the case of injection of $CCl_4$, the composition of the liver tissue was irregular and the degree of damage was severe, the accumulation of collagen was observed, the generation and accumulation of Ccl20 and Cxcl10 were observed, the infiltration of (F4/80 positive) macrophages was prominent, and the accumulation of laminin γ2 was observed. However, as shown in FIGS. 6A to 6D, the effect of $CCl_4$ treatment was significantly inhibited according to the additional injection of Ccl20 siRNA (siCcl20) for the Ccl20 expression suppression. Meanwhile, the mRNA levels of collagen type 1 α1 chain (Col1α1), Ccl20, F4/80, and α-smooth muscle actin (Sma) were also increased by the treatment of CCl$_4$, and the levels were decreased when the expression of Ccl20 was suppressed during the CCl$_4$ treatment. Therefore, it was confirmed that suppressing the expression of Ccl20 inhibited inflammation (increased expression of Ccl20 and Cxcl10 and increased degree of F4/80 staining) and fibrosis (increased expression of α-Sma, collagen and laminin γ2) of the liver induced by the treatment of CCl$_4$.

Experimental Example 4: Activation of M1 Type Macrophages that Induce Inflammation by Improving Glycolysis of Macrophages Dependent on TM4SF5 Expression: Confirmation of Interaction Between Hepatic Epithelial Cells and Macrophages by TM4SF5 Expression <4-1> Confirmation of Binding of TM4SF5 and Glut1

THP-1 cell line was transfected with expression plasmids for TM4SF5-Strep (control vector, WT, N-Glycosylation-deficient mutant; N138A/N155Q), Palmitoylation-deficient mutant (C2/6/9/75/76/80/81/85/189A), Glut1 (accession number: NP_006507) WT, Glut1 K38A, and Glut1 E329Q, and after 48 hours, cell extracts were obtained. The binding of TM4SF5 and Glut1 was confirmed by Western blotting of Glut-HA using an anti-HA antibody by pulling-down with strepavidin agarose resin (Thermo Fisher Scientific).

Figure 7:
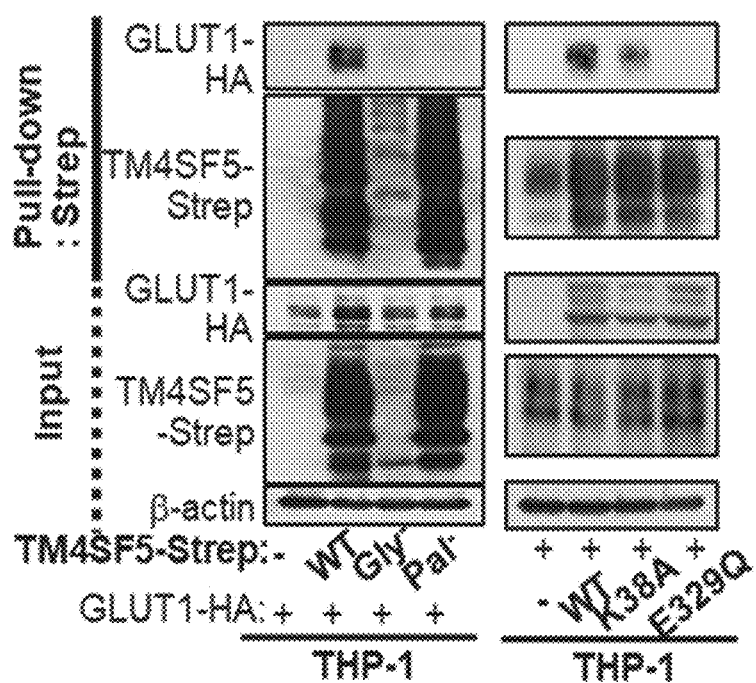
FIG. 7 is a set of photographs showing the results of confirming the binding of TM4SF5 and Glut1.

As a result, as shown in FIG. 7, WT TM4SF5 was bound to WT Glut1, and when TM4SF5 was a mutant in which N-glycosylation or palmitoylation did not occur, it was not bound. When Glut1 was a mutant of K38A, the binding was weakened, but E328Q mutant whose structure was changed by mutation of E328 located in the cytoplasm to Q328 did not bind. Therefore, it was estimated that TM4SF5 could help glucose uptake by binding to Glut1.

<4-2> Measurement of Activation of Glycolytic Function According to TSAHC Treatment The cells expressing TM4SF5 were treated with vehicle, a negative control compound (4'-methoxy-4-dihydroxychalcone) or TSAHC. Then, the degree of activation of glycolytic function was measured by measuring the acidification of the extracellular solution due to glycolysis while additionally adding glucose at various concentrations using Seahorse equipment.

Figure 8A:
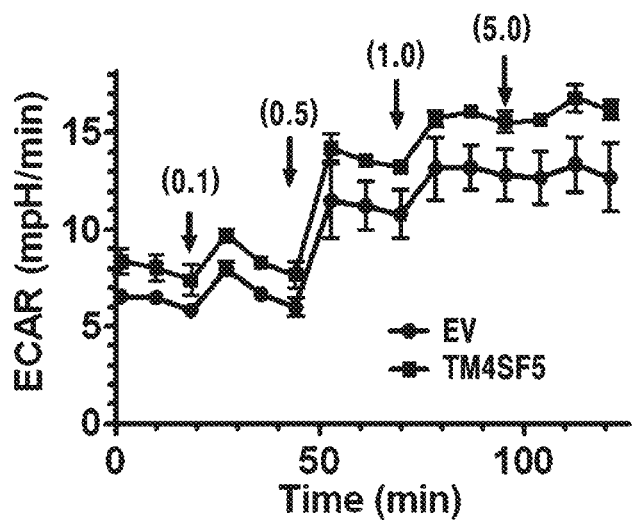
FIG. 8 is a set of graphs showing the results of measuring the activation degree of glycolytic function in a cell line transformed with EV or TM4SF5 (A), an EV-expressing cell line treated with vehicle, negative control compound (4'-methoxy-4-dihydroxychalcone) or TSAHC (B), and a TM4SF5-expressing cell line treated with vehicle, negative control compound (4'-methoxy-4-dihydroxychalcone) or TSAHC (C).
Figure 8B:
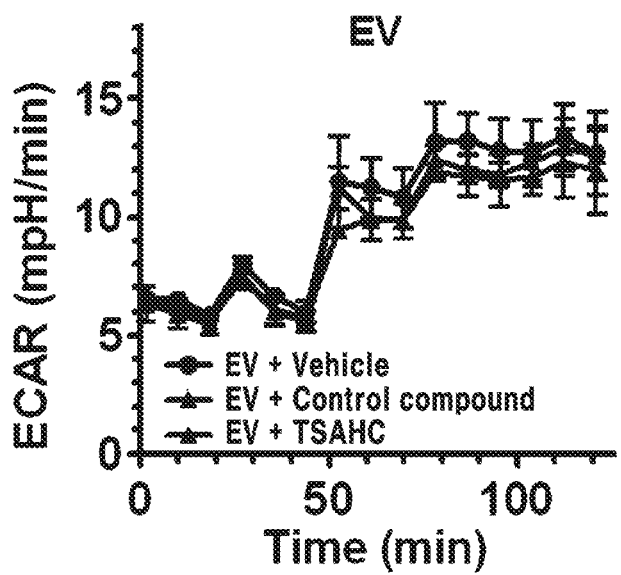
Figure 8C:
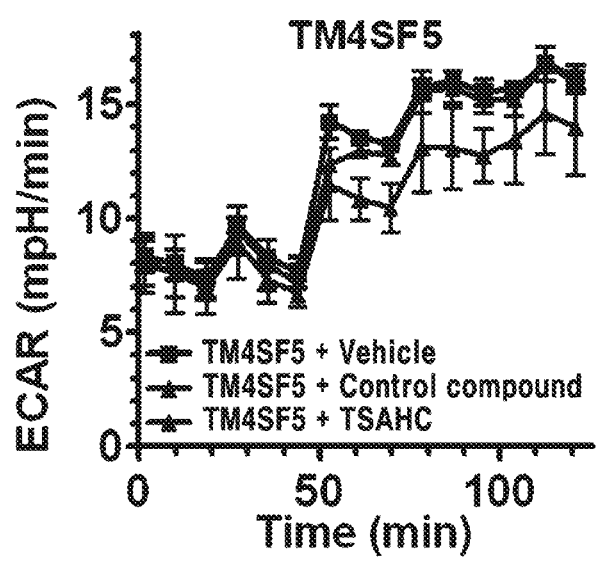
Figure 9A:
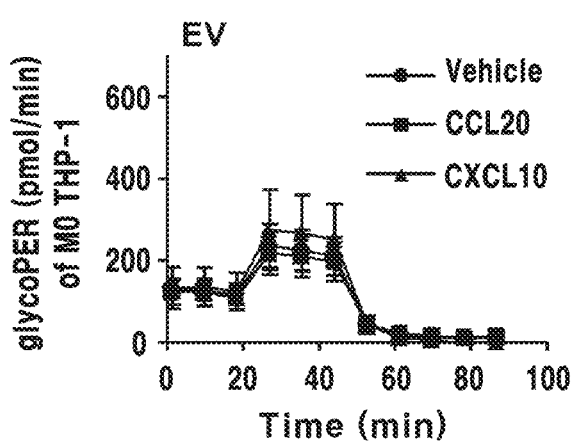
FIG. 9 is a set of graphs showing the results of measuring basal (C) and compensatory Glycolytic Proton Efflux Rate (GlycoPER) (D) by treating CCL20 or CXCL10 in THP-1 cells infected with lentivirus expressing EV (A) or TM4SF5 (B).
Figure 9B:
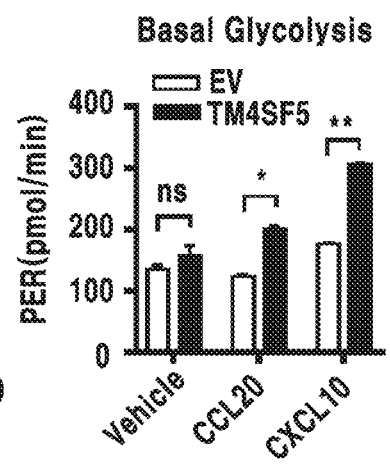
Figure 9C:
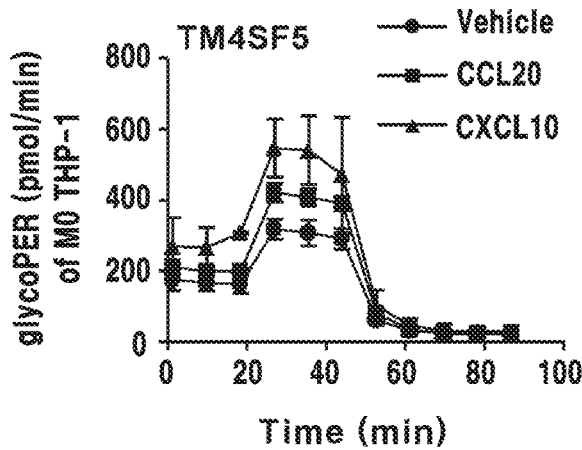
Figure 9D:
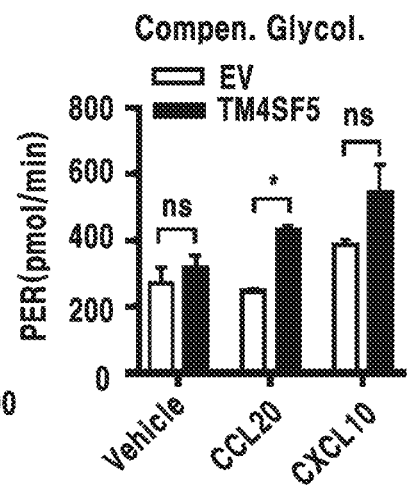

As a result, as shown in FIGS. 8A to 8C, the cells expressing TM4SF5 showed higher glycolytic function even under the condition of adding various concentrations of glucose than the cells not expressing TM4SF5 (EV), which was not changed by the treatment of a control compound but decreased by the treatment of TSAHC. In particular, glycolysis of the cells not expressing TM4SF5 was not changed despite the treatment of a control compound and TSAHC.

Therefore, through Experimental Examples <4-1> and <4-2>, it was found that the TM4SF5 expressed in macrophages binds to Glut1 and helps the absorption of glucose into cells, thereby promotes glycolysis.

<4-3> Measurement of Activation of Glycolytic Function in M0 Cells According to TSAHC Treatment and TM4SF5 Expression THP-1 cells infected with a lentivirus with an empty vector not expressing TM4SF5 or a lentivirus expressing TM4SF5 were treated with 100 nM phorbol-12-myristate-13-acetate (PMA) for 24 hours to differentiate into M0 cells (experimental condition to confirm the not repetitive effects of cytokines/chemokines in the early stage by representing the case before differentiation into M1 type), and then, 300 ng/ml of CCL20 or CXCL10 was treated for 24 hours, and basal and compensatory Glycolytic Proton Efflux Rate (GlycoPER) were measured using a Seahorse XFp device.

As a result, as shown in FIGS. 9A to 9D, the glycolytic function was much higher in M0 THP-1 cells expressing TM4SF5 than in M0 THP-1 cells not expressing TM4SF5, and the glycolytic function in M0 THP-1 cells expressing TM4SF5 was higher than that of the vehicle-treated control group due to the additional treatment of CCL20 or CXCL10.

<4-4> Confirmation of Binding of TM4SF5 and IL6-Ra and Inhibition of Binding by TSAHC Treatment Hepatic epithelial cells were infected with an empty vector (EV) or lentivirus expressing TM4SF5, and TSAHC was not treated (−) or treated (+) thereto. A cell extract was obtained, and TM4SF5-Strep was precipitated using strepavidin-agarose beads, and then Western blotting was performed with the IL-6 receptor, IL-6Rα antibody.

Figure 10:
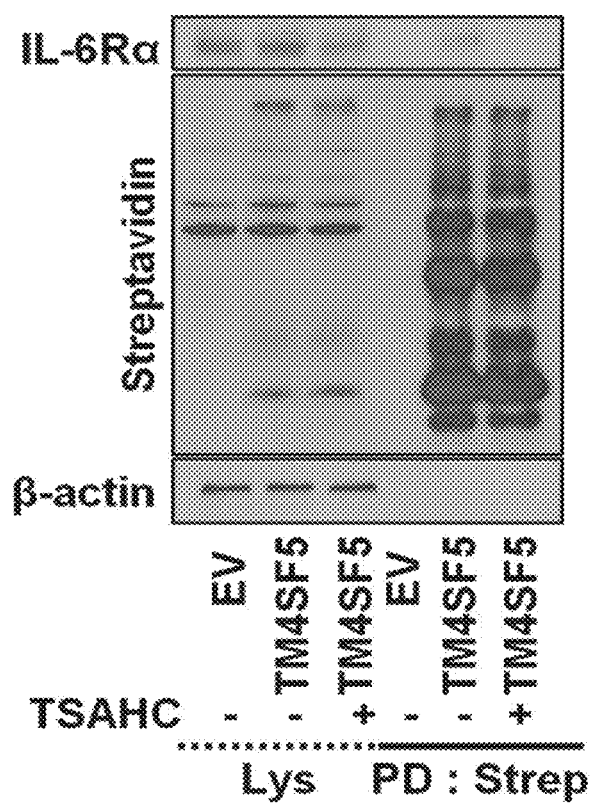
FIG. 10 is a set of photographs showing the results of confirming the binding of TM4SF5 and IL6-Ra and the binding inhibition according to the treatment of TSAHC.

As a result, as shown in FIG. 10, it was confirmed that TM4SF5 and IL6-Rα were bound, and that this binding was also inhibited by the treatment of TSAHC.

<4-5> Confirmation of Changes in mRNA Expression of CCL2, TNF-α, IL-6 and IL-1β According to TSAHC Treatment Cell lines not expressing TM4SF5 (EV) or cell lines expressing thereof (TM4SF5) were treated (+) or not treated with LPS and IFN-γ, treated (+) or not treated with 2-DG (2-Deoxy-D-glucose) as a drug for inhibiting glycolysis at a given concentration, and additionally treated (+) or not treated with TSAHC (−). Then, the mRNA expression levels of CCL2, TNF-α, IL-6, and IL-1β, the chemokines/cytokines indicating the activation of M1-type macrophages, were confirmed by qRT-PCR.

As a result, as shown in FIGS. 11A to 11D, the mRNA expression levels of CCL2, TNF-α, IL-6, and IL-1β were higher in the cell line expressing TM4SF5 than in the cell lines not expressing TM4SF5, and the levels were decreased by the treatment of 2-DG or TSAHC.

Experimental Example 5: Confirmation of mRNA Expression Levels of Markers Indicating Activity as M1 or M2 Type Macrophages According to CCL20 or CXCL10 Treatment in Macrophages Differentiated from THP-1 Cells M1 and M2 type macrophages (MΦ) differentiated from THP-1 cells were treated with CCL20 or CXCL10 at a concentration of 100 nM for 24 hours, and then the mRNA expression levels of the markers indicating the activity as M1 or M2 type macrophages were confirmed by qRT-PCR. For M1 type macrophages, the mRNA expression levels of TNFα, IL1β and IL6 were measured, and for M2 type macrophages, the mRNA expression levels of CD206 and FN1 were measured.

Figure 12A:
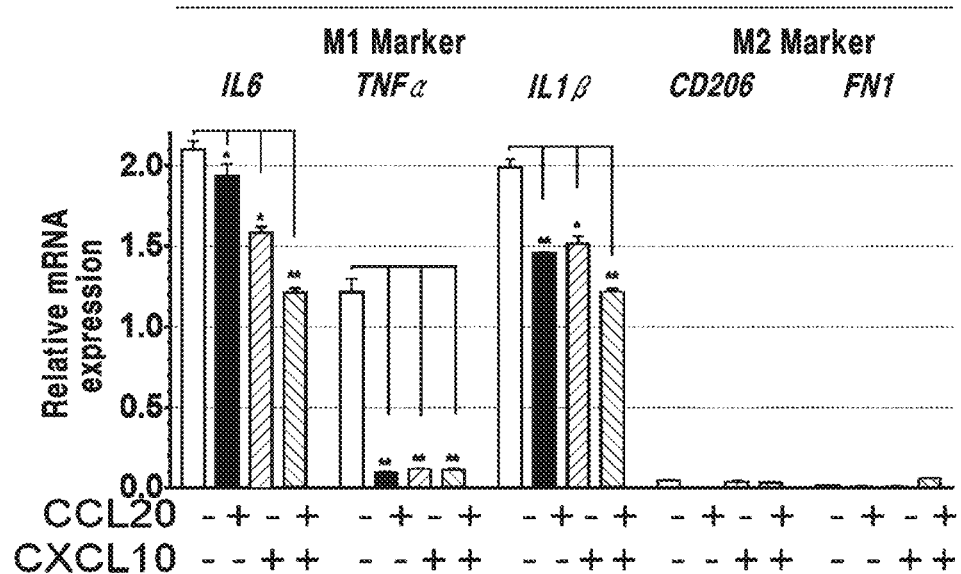
FIG. 12 is a set of graphs showing the results of confirming the mRNA expression levels of the M1 or M2 type macrophage markers according to the treatment of CCL20 or CXCL10 in macrophages differentiated into M1 (A) or M2 (B) from THP-1 cells.
Figure 12B:
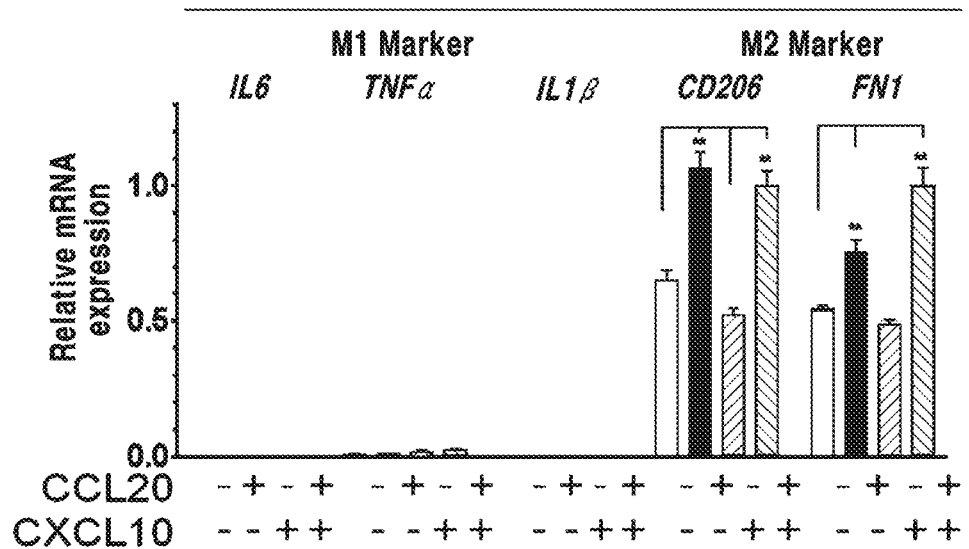

As a result, as shown in FIGS. 12A and 12B, the mRNA levels of M1 type macrophage markers were decreased compared to the control group when M1 type macrophages were treated with CCL20 or CXCL10, respectively or together. On the other hand, when M2 type macrophages were treated with CCL20 alone or together with CXCL10, the mRNA levels of M2 type macrophage markers were significantly increased.

Experimental Example 6: Confirmation of Effect on Macrophage Activity in Liver Injury Model of Tm4sf5 Gene-Deficient Mice <6-1> Confirmation of mRNA Expression Levels of Markers Indicating Activity as M1 or M2 Type Macrophages in Macrophages Differentiated from BMDM Cells Using Methionine-Choline Deficient Mouse Model Normal mice (WT) or Tm4sf5 gene-deficient mice (KO) were allowed to freely eat the normal diet or the methionine-choline deficient (MCD) diet for 4 weeks. Bone marrow-derived macrophages (BMDM) were isolated from each animal group and differentiated into M0, M1, or M2 for 24 hours. Then, the mRNA levels of M1 macrophage markers (Ccl2, Tnfa and Il-6) or M2 macrophage marker (Arg1) were confirmed by qRT-PCR.

As a result, as shown in FIGS. 13A to 13D, the M1 macrophage markers were increased in the bone marrow-derived macrophages of WT mice according to MCD compared to the control group. On the other hand, in the bone marrow-derived macrophages of KO mice, the M2 macrophage marker was increased. That is, the above results suggest that macrophages can be activated by causing chronic inflammation in the case of MCD.

<6-2> Confirmation of Liver Tissue Damage According to Tm4sf5 Gene Expression Using Methionine-Choline Deficient Mouse Model Normal mice (WT) or Tm4sf5 gene-deficient mice (KO) were allowed to freely eat the normal diet (Chow) or the methionine-choline deficient (MCD) diet for 4 weeks. Liver tissues were obtained from each animal group, and the state of the liver tissue and the fat accumulation was confirmed by H&E staining, the degree of the fat accumulation was confirmed by Oil-Red O staining, and the collagen accumulation was confirmed by Masson's Trichrome staining.

Figure 14:
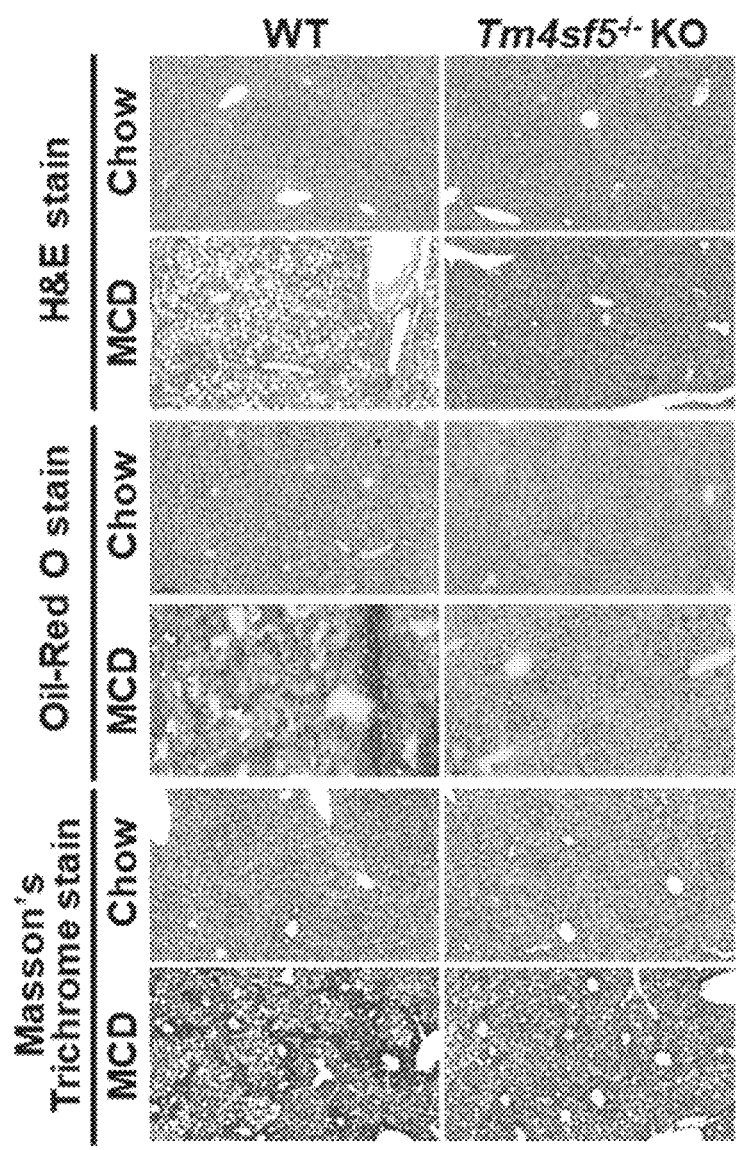
FIG. 14 is a set of photographs showing the results of confirming the liver tissue damage, fat accumulation, and collagen accumulation according to the Tm4sf5 gene expression using a methionine-choline deficient mouse model.

As a result, as shown in FIG. 14, it was confirmed that the accumulation of fat and the synthesis/accumulation of collagen were excessive according to MCD in the liver tissue of WT mice compared to the control group, and the symptoms of steatohepatitis accompanied by liver fibrosis were induced. On the other hand, it was confirmed that such phenomena occurred insignificantly in the liver tissue of KO mice.

<6-3> Confirmation of Expression Levels of F4/80, Ccl20 and Cxcl10 in Liver Tissue According to Tm4sf5 Gene Expression Using Methionine-Choline Deficient Mouse Model Normal mice (WT) or Tm4sf5 gene-deficient mice (KO) were allowed to freely eat the normal diet (Chow) or the methionine-choline deficient (MCD) diet for 4 weeks. Liver tissues were obtained from each animal group and immunochemotherapy was performed using F4/80, Ccl20 and Cxcl10 antibodies.

Figure 15:
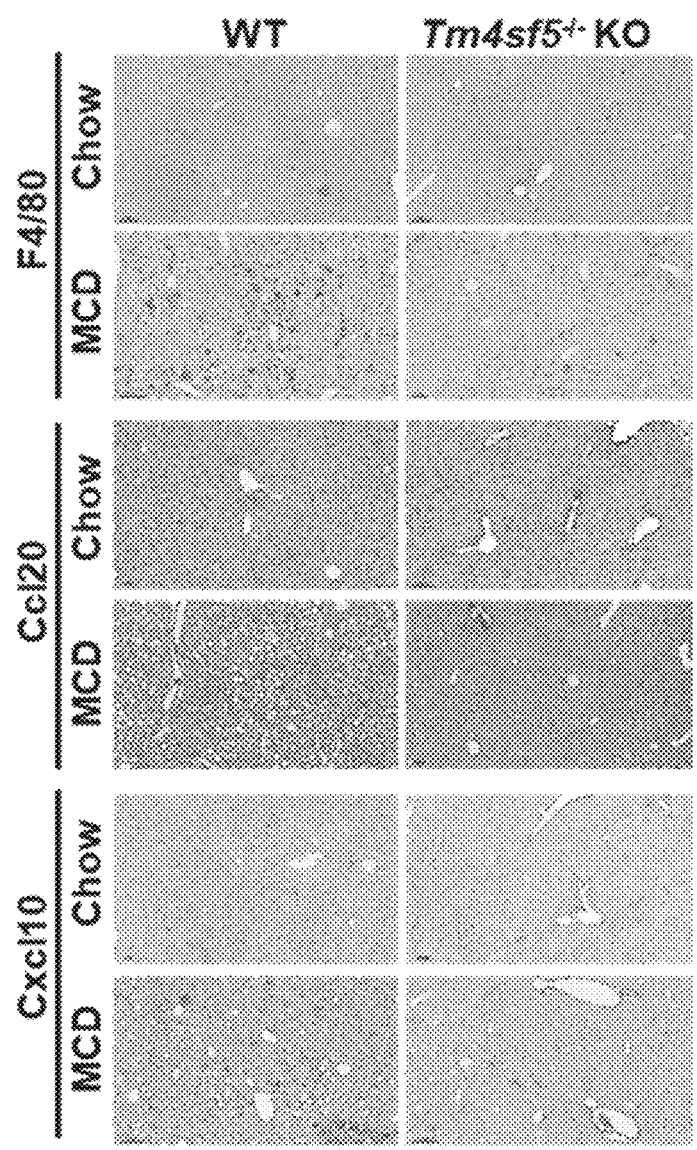
FIG. 15 is a set of photographs showing the results of confirming the expression levels of F4/80, Ccl20 and Cxcl10 in the liver tissue according to the Tm4sf5 gene expression using a methionine-choline deficient mouse model.

As a result, as shown in FIG. 15, compared to the control group, it was confirmed that the macrophages stained with F4/80 were excessively concentrated in the liver tissue of WT mice according to MCD, and that the synthesis/secretion of Ccl20 and Cxcl10 was induced. On the other hand, it was confirmed that such phenomena occurred insignificantly in the liver tissue of KO mice.

<6-4> Confirmation of Liver Damage (H&E Staining) According to Tm4sf5 Gene Expression Using Methionine-Choline Deficient Mouse Model Normal mice (WT) or Tm4sf5 gene-deficient mice (KO) were allowed to freely eat the normal diet (Chow) or the methionine-choline deficient (MCD) diet for 4 weeks. Liver tissues were obtained from each animal group and H&E staining was performed.

Figure 16:
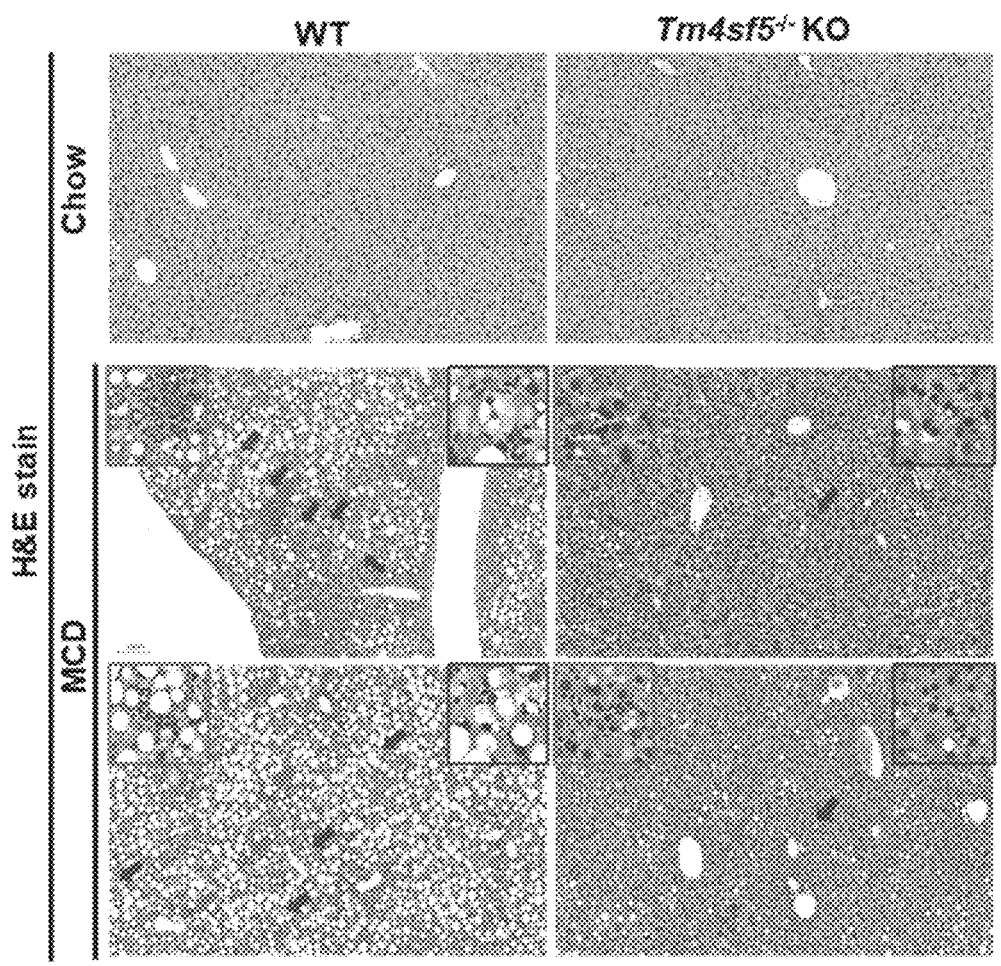
FIG. 16 is a set of photographs showing the results of confirming the liver damage and immune cell density through ballooning of hepatic epithelial cells according to the Tm4sf5 gene expression using a methionine-choline deficient mouse model.

As a result, as shown in FIG. 16, compared to the control group, it was confirmed that the excessive accumulation of fat and the concentration of immune cells (red box and arrow) were induced in the liver tissue of WT mice according to MCD, and that ballooning (blue box and arrow) was increased due to damage of hepatocytes. On the other hand, it was confirmed that such phenomena occurred insignificantly in the liver tissue of KO mice.

<6-5> Confirmation of Expression Level of F4/80 in Liver Tissue According to Tm4sf5 Gene Expression Using High-Fat Diet Mouse Model Normal mice (WT) or Tm4sf5 gene-deficient mice (KO) were allowed to freely eat AIN or HFD for 15 weeks. Liver tissues were obtained from each animal group and immunochemotherapy was performed using F4/80 antibody.

Figure 17A:
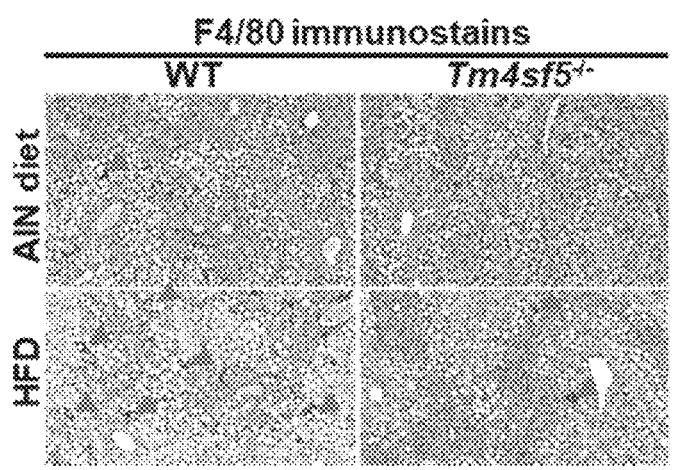
FIG. 17 is a set of photographs and a graph showing the results of F4/80 immunohistochemical staining (A) and the results of confirming the number of crown-like structure (CLS) in which immune cells are concentrated (B) in the liver tissue according to the Tm4sf5 gene expression using a high-fat diet mouse model.
Figure 17B:
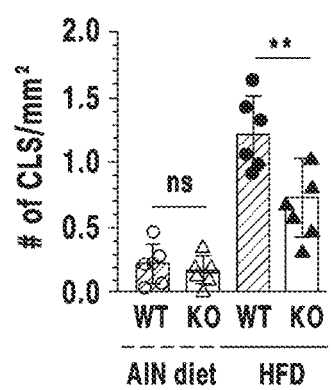

As a result, as shown in FIGS. 17A and 17B, Unlike the control AIN condition, it was confirmed that the excessive concentration of macrophages stained with F4/80 occurred in the liver tissue of WT mice according to HFD, and the number of CLS (crown-like structure), a clustering phenomenon of immune cells, was also increased. On the other hand, it was confirmed that such phenomena occurred insignificantly in the liver tissue of KO mice.

<6-6> Confirmation of mRNA Expression Level of Markers Indicating Presence and Activity of Kupffer Macrophages According to Tm4sf5 Gene Expression Using Methionine-Choline Deficient Mouse Model Normal mice (WT) or Tm4sf5 gene-deficient mice (KO) were allowed to freely eat the normal diet (Chow) or the methionine-choline deficient (MCD) diet for 4 weeks. Liver tissues were obtained from each animal group and qRT-PCR was performed to confirm the mRNA expression levels of Trem2 (triggering receptor expressed on myeloid cells), Clec4f (C type lectin domain family 4 member F) and Tim4 (T-cell immunoglobulin and mucin domain containing 4), the markers indicating the presence and activity of Kupffer macrophages.

As a result, as shown in FIGS. 18A to 18D, compared to the control group, it was confirmed that the mRNA expression levels of Trem4, Clec4f and Tim4 were high in the liver tissues of WT mice fed with MCD. On the other hand, it was confirmed that such phenomena occurred insignificantly in the liver tissue of KO mice. The above results suggest that Kupffer macrophages were present in the liver tissue of WT mice and that their activity was strong according to MCD.

Experimental Example 7: Inhibition of Liver Damage, Inflammation and Fibrosis Caused by $CCl_4$ Treatment According to TSAHC Treatment, which Inhibits TM4SF5 Activity <7-1> Confirmation of Increase of Tm4sf5 mRNA Expression Level, ALT Level, and Liver Tissue Weight and Body Weight in Mouse Model that can be Accompanied by Cell Damage and Inflammation when Liver Fibrosis is Induced by $CCl_4$ Treatment, and Decrease of the Corresponding Levels According to TSAHC Treatment In a mouse animal model that can be accompanied by cell damage and inflammation when liver fibrosis is induced by the treatment of $CCl_4$, the animal groups periodically treated (+) or not treated (−) with TSAHC during the $CCl_4$ treatment were obtained. The body weight during 4 weeks of the treatment and the liver tissue weight after 4 weeks were calculated as a ratio (liver/body weight), or the ALT liver levels were measured from blood samples. The liver tissue was obtained and Tm4sf5 mRNA was measured by qRT-PCR.

Figure 19A:
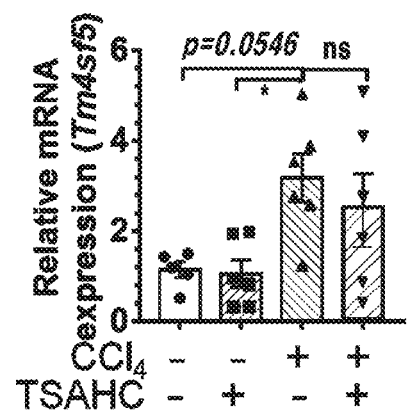
FIG. 19 is a set of graphs showing the results of confirming the Tm4sf5 mRNA expression level (A), ALT level (B), and liver tissue weight and body weight (C) according to the treatment of TSAHC in a mouse model that can be accompanied by cell damage and inflammation when liver fibrosis is induced by the treatment of $CCl_4$.
Figure 19B:
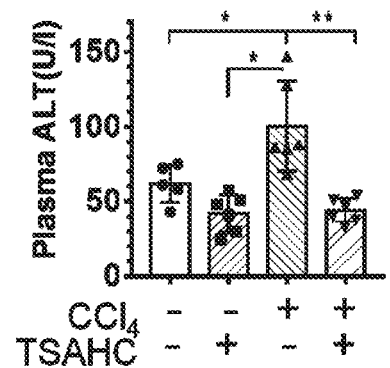
Figure 19C:
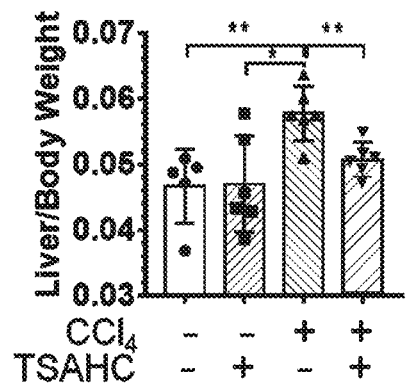

As a result, as shown in FIGS. 19A to 19C, it was confirmed that the Tm4sf5 mRNA expression level, ALT level, and liver tissue weight and body weight were all increased in the group treated with $CCl_4$ compared to the group not treated with CCl$_4$, and these values were decreased by the treatment of TSAHC.

<7-2> Confirmation of Liver Injury in Mouse Model that can be Accompanied by Cell Damage and Inflammation when Liver Fibrosis is Induced by CCl$_4$ Treatment, and Decrease of Liver Injury According to TSAHC Treatment In an animal model treated with CCl$_4$ to induce liver fibrosis, the animal groups periodically treated (+) or not treated (−) with TSAHC during the CCl$_4$ treatment were obtained. After 4 weeks of the treatment, the liver tissue was obtained and H&E and Masson's trichrome staining was performed.

Figure 20:
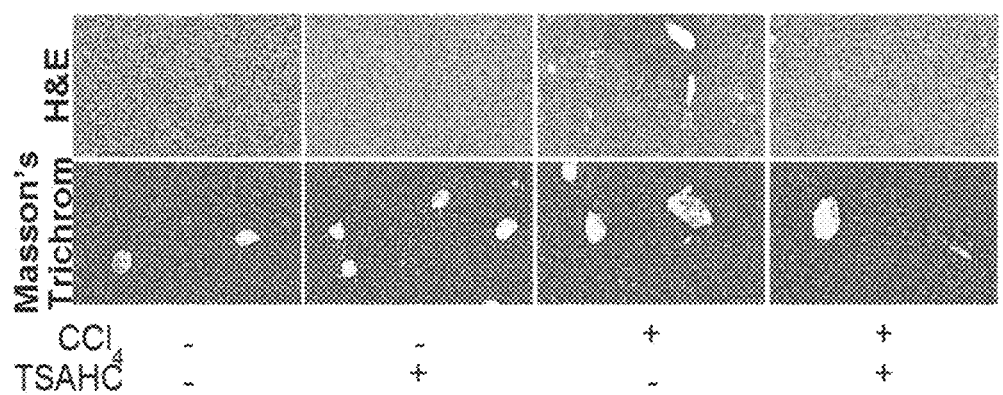
FIG. 20 is a set of photographs showing the results of confirming the liver damage according to the treatment of TSAHC in a mouse model that may be accompanied by cell damage and inflammation when liver fibrosis is induced by the treatment of $CCl_4$.
Figure 21A:
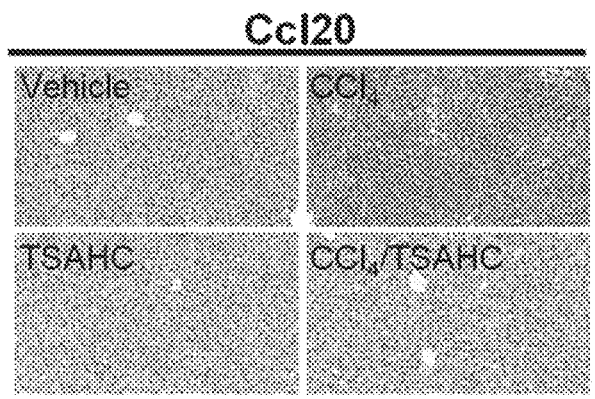
FIG. 21 is a set of photographs and graphs showing the results of immunostaining of Ccl20 and Cxcl10 (A or B) and the results of confirming the relative mRNA expression level (C or D) in the liver tissue of a mouse model that can be accompanied by cell damage and inflammation when liver fibrosis is induced by the treatment of $CCl_4$.
Figure 21B:
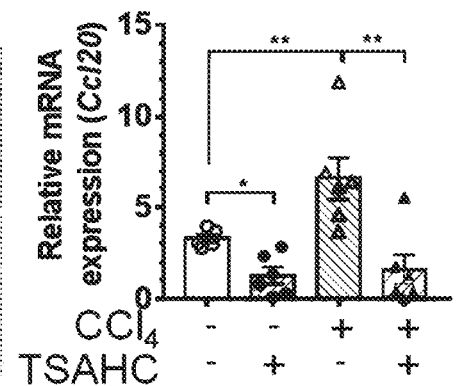
Figure 21C:
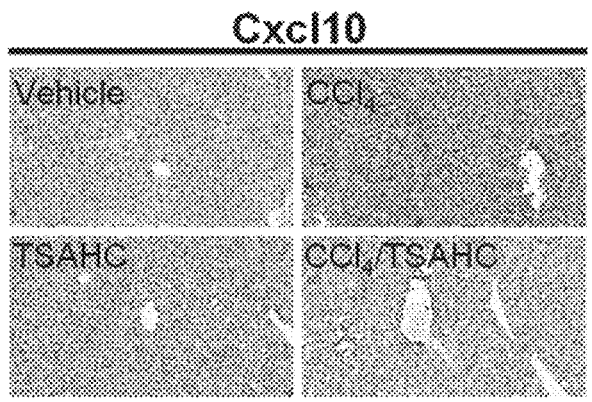
Figure 21D:
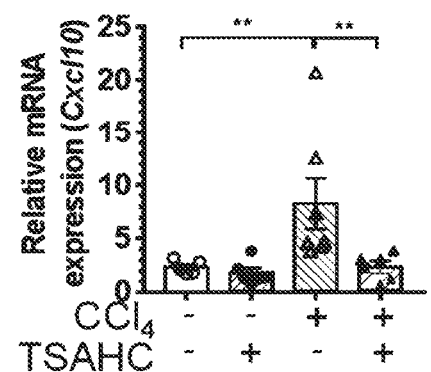

As a result, as shown in FIG. 20, it was confirmed that the degree of liver tissue damage was greater or the cell composition was irregular, and the collagen accumulation was prominent in the group treated with CCl$_4$, compared to the group not treated with CCl$_4$, and these phenomena were decreased by the treatment of TSAHC.

<7-3> Confirmation of Increase of mRNA Expression of Ccl20 and Cxcl10 in Mouse Model that can be Accompanied by Cell Damage and Inflammation when Liver Fibrosis is Induced by CCl$_4$ Treatment, and Decrease of the Expression According to TSAHC Treatment In an animal model treated with CCl$_4$ to induce liver fibrosis, the animal groups periodically treated (+) or not treated (−) with TSAHC during the CCl$_4$ treatment were obtained. After 4 weeks of the treatment, the liver tissue was obtained and immunostaining was performed for Ccl20 and Cxcl10.

As a result, as shown in FIGS. 21A to 21D, the mRNA expression levels of Ccl20 and Cxcl10 were significantly higher in the group treated with CCl$_4$ compared to the group not treated with CCl$_4$. However, the mRNA expression levels of Ccl20 and Cxcl10 were decreased by the treatment of TSAHC.

<7-4> Confirmation of Decrease of Macrophage Marker F4/80 mRNA Expression in Mouse Model that can be Accompanied by Cell Damage and Inflammation when Liver Fibrosis is Induced by CCl$_4$ Treatment According to F4/80 Immunostaining and TSAHC Treatment In a mouse model that can be accompanied by cell damage and inflammation when liver fibrosis is induced by CCl$_4$ treatment, the animal groups periodically treated (+) or not treated (−) with TSAHC during the CCl$_4$ treatment were obtained. After 4 weeks of the treatment, the liver tissue was obtained and immunostaining was performed for F4/80, a macrophage marker.

Figure 22A:
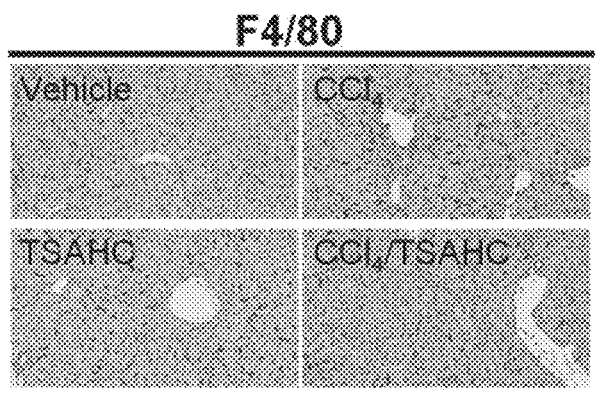
FIG. 22 is a set of photographs and a graph showing the results of immunostaining of the macrophage marker F4/80 (A), and the results of confirming the F4/80 mRNA expression level (B) according to the treatment of TSAHC in a mouse model that can be accompanied by cell damage and inflammation when liver fibrosis is induced by the treatment of $CCl_4$.
Figure 22B:
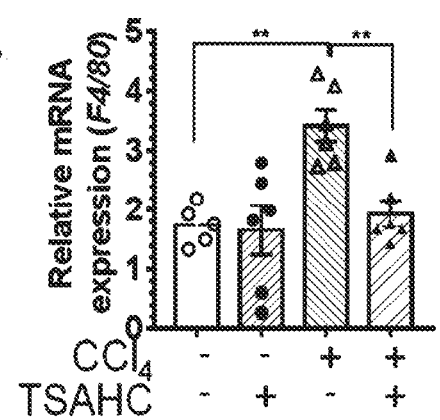

As a result, as shown in FIGS. 22A and 22B, the staining of immune cell macrophages was more prominent in the group treated with CCl$_4$ than in the group not treated with CCl$_4$. In addition, it was confirmed that the F4/80 mRNA expression was increased in the group treated with CCl$_4$ compared to the group not treated with CCl$_4$, but the F4/80 mRNA expression was decreased by the treatment of TSAHC.

<7-5> Confirmation of Decrease of α-SMA mRNA Expression in Mouse Model that can be Accompanied by Cell Damage and Inflammation when Liver Fibrosis is Induced by CCl$_4$ Treatment According to α-SMA Immunostaining and TSAHC Treatment In a mouse model that can be accompanied by cell damage and inflammation when liver fibrosis is induced by CCl$_4$ treatment, the animal groups periodically treated (+) or not treated (−) with TSAHC during the CCl$_4$ treatment were obtained. After 4 weeks of the treatment, the liver tissue was obtained and immunostaining was performed for α-SMA indicating the activation of hepatic stellate cells.

Figure 23A:
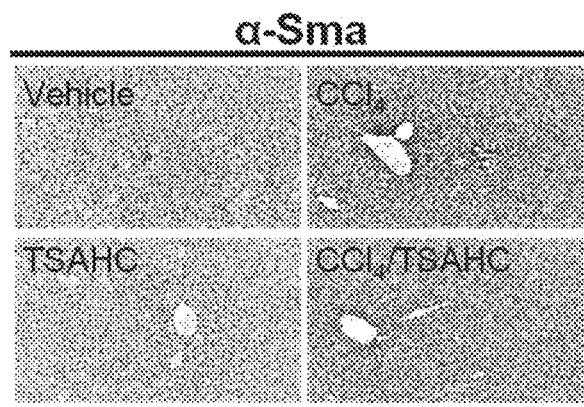
FIG. 23 is a set of photographs and a graph showing the results of α-SMA immunostaining (A), and the results of confirming the α-SMA mRNA expression level (B) according to the treatment of TSAHC in a mouse model that can be accompanied by cell damage and inflammation when liver fibrosis is induced by the treatment of $CCl_4$.
Figure 23B:
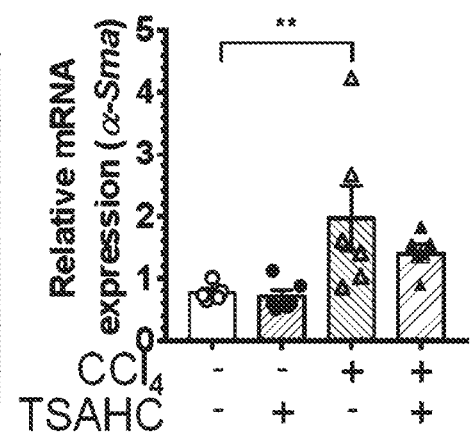

As a result, as shown in FIGS. 23A and 23B, the expression of α-SMA was remarkably high in the group treated with CCl$_4$ than in the group not treated with CCl$_4$, indicating the activation of hepatic stellate cells. In addition, it was confirmed that the expression of α-SMA mRNA was increased in the group treated with CCl$_4$ compared to the group not treated with CCl$_4$, but the expression of α-SMA mRNA was decreased by the treatment of TSAHC.

Experimental Example 8: Confirmation of Inhibition of Liver Inflammation and Fibrosis by CCl$_4$ Treatment According to Inhibition of Collagen I and Laminin γ2 Expression Dependent on TM4SF5 Expression <8-1> Confirmation of Decrease of Immune Cell Recruit in Liver Tissue According to Inhibition of Collagen I and Laminin γ2 Expression Dependent on Tm4sf5 mRNA Expression Through Tissue Staining in Mouse Model that can be Accompanied by Cell Damage and Inflammation when Liver Fibrosis is Induced by CCl$_4$ Treatment While a mouse model that can be accompanied by cell damage and inflammation when liver fibrosis is induced by CCl$_4$ treatment was treated with CCl$_4$, control siRNA, Lamc2 (laminin γ2 chain) siRNA and Col1a (collagen type 1 α chain) siRNA were injected intravenously every 4 days. After 22 days of the injection, the liver tissue was obtained and the degree of liver tissue damage was confirmed by H&E staining.

Figure 24:
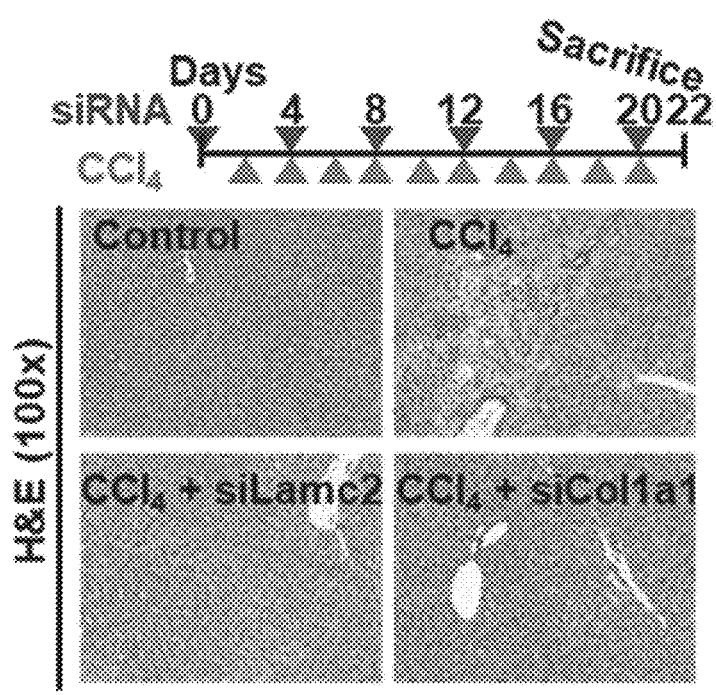
FIG. 24 is a set of photographs showing the results of confirming the degree of liver damage and immune cell recruit by injecting siCol1a1 or siLamc2 into the tail vein in a mouse model that can be accompanied by cell damage and inflammation when liver fibrosis is induced by the treatment of $CCl_4$.

As a result, as shown in FIG. 24, the liver tissue irregularity, damage, and inflammation (infiltration of immune cells) were more prominent in the group treated with CCl$_4$ than in the group not treated with CCl$_4$. In addition, it was confirmed that these results were decreased as the expression of collagen I and laminin γ2 was suppressed, respectively.

<8-2> Confirmation of Decrease of STAT3 Tyrosine 705 Phosphorylation Associated with Inflammation in Liver Tissue According to Inhibition of Collagen I and Laminin γ2 Expression Dependent on Tm4sf5 mRNA Expression Through Western Blotting in Mouse Model that can be Accompanied by Cell Damage and Inflammation when Liver Fibrosis is Induced by CCl$_4$ Treatment While an animal model treated with CCl$_4$ to induce liver inflammation and fibrosis was treated with CCl$_4$, control siRNA, Lamc2 (laminin γ2 chain) siRNA and Col1a (collagen type 1 α chain) siRNA were injected intravenously every 4 days. After 22 days of the injection, the liver tissue was obtained and the expression levels of the proteins indicated in the liver tissue were confirmed through various western blotting.

Figure 25:
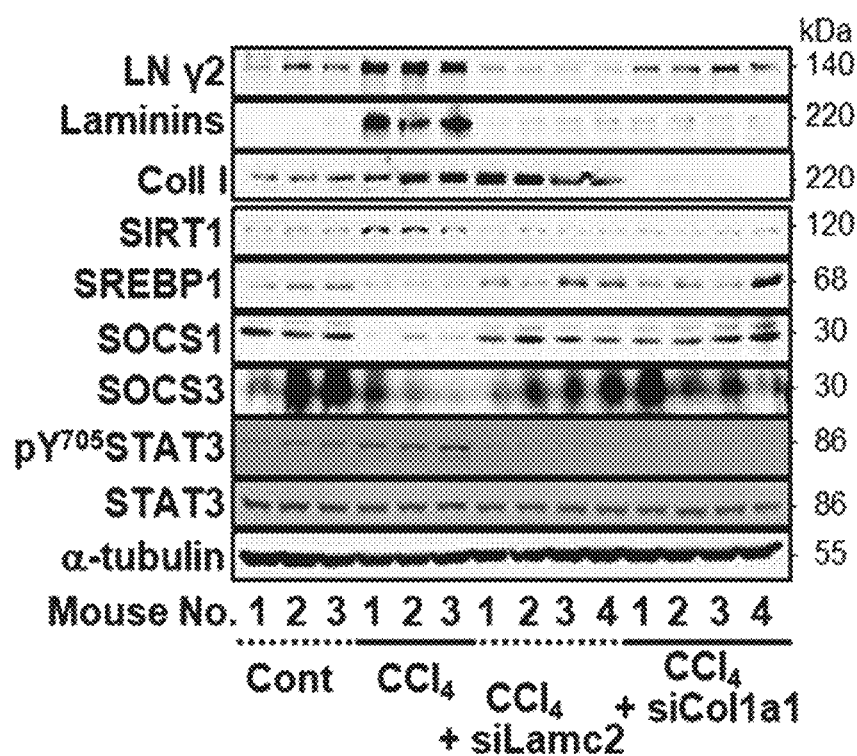
FIG. 25 is a set of photographs showing the results of confirming the phosphorylation level of Tyr705 of STAT3 increased according to the treatment of $CCl_4$ by suppressing the expression of laminin γ2 and collagen 1 alpha1 in a mouse model that can be accompanied by cell damage and inflammation when liver fibrosis is induced by the treatment of $CCl_4$.

As a result, as shown in FIG. 25, the expression of collagen I, laminin γ2 (LN γ2), laminin, and SIRT1 and the phosphorylation of STAT3 Tyr705, a characteristic of M2-type macrophages, were increased, and SREBP1, SOCS1 and SOCS3 were decreased in the group treated with CCl$_4$ than in the group not treated with CCl$_4$. It was confirmed that the effect of CCl$_4$ was reversed by suppressing the expression of collagen I and laminin γ2, respectively.

Experimental Example 9: Effect of TM4SF5 Expression on Keap1 Expression and Antioxidation SNU449 cells that do not natively express TM4SF5 were transformed with the control empty vector (EV) or TM4SF5. Keap1 expression vector was additionally injected into the cells, and qRT-PCR was performed to confirm the mRNA levels of the indicated cytokines/chemokines using these cells.

Figure 26:
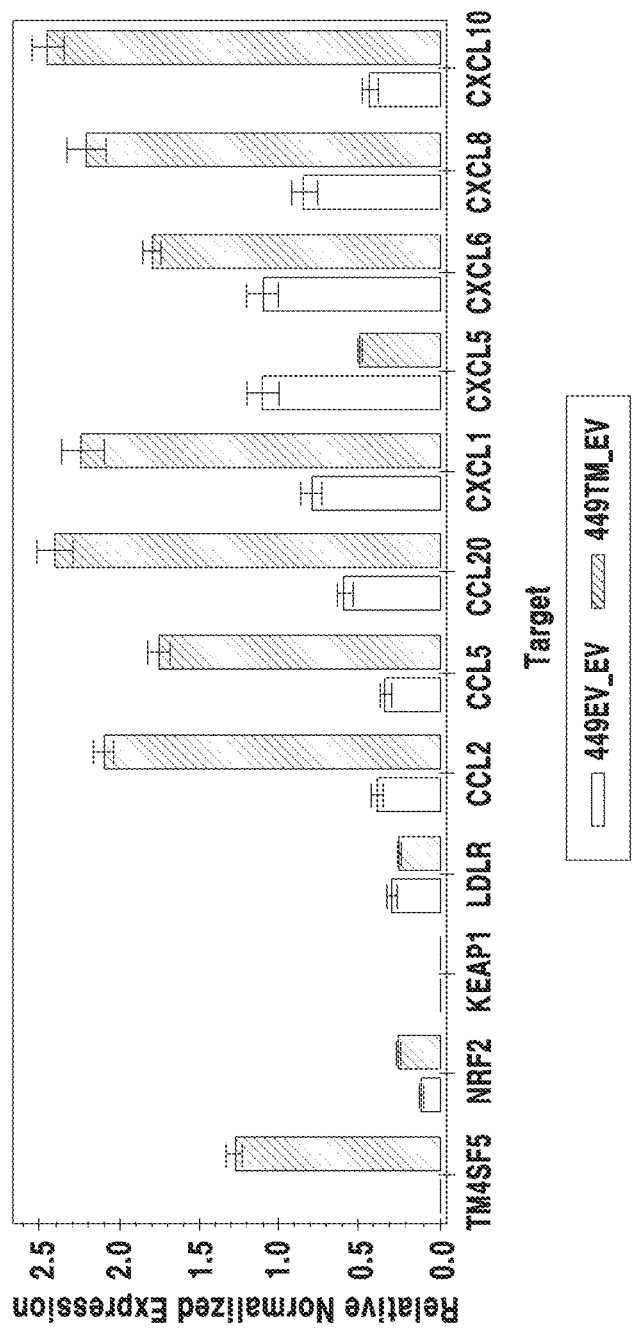
FIG. 26 is a graph showing the results of confirming the mRNA levels of cytokines/chemokines according to the expression of TM4SF5 or Keap1 (Kelch Like ECH Associated Protein 1) using SNU449 cell line.

As a result, as shown in FIG. 26, it was confirmed that the expression of chemokines such as CCL2, CCL5, CCL20, CXCL1, CXCL6, CXCL8 and CXCL10 increased by the expression of TM4SF5 was decreased by the additional expression of KEAP1. That is, it was confirmed that the TM4SF5 expression-dependent cytokine/chemokine expression can be regulated in such a way that Keap1 suppresses thereof.

What is claimed is:

1. An immunosuppressive method, comprising:
   administering 4'-(p-toluenesulfonylamido)-4-hydroxychalcone (TSAHC) to a subject in an amount effective for the TSAHC to inhibit:
   (i) secretion of inflammatory cytokines or chemokines dependent on the expression of TM4SF5;
   (ii) activation of M1 type macrophages by inhibiting (a) binding of TM4SF5 and GLUT1, (b) sensitivity of glycolysis to extracellular glucose, or (c) glycolysis in macrophages;
   (iii) conversion of M1 type macrophages to M2 type macrophages; and
   (iv) chronic activation of M2 type macrophages by inhibiting the expression of mannose receptor C-type 1 (MRC1, CD206), fibronectin (FN1), arginase I (Arg1), and peroxisome proliferator-activated receptor gamma (Pparγ) in macrophages,
   in the subject, thereby suppressing immunity in the subject,
   wherein the subject has excessive inflammatory response caused by liver resection or liver tissue resection, abnormality in metabolic function of liver or liver tissue, liver transplant rejection or liver tissue transplant rejection, or exposure to substance (s) toxic to the liver or liver tissue.

2. The immunosuppressive method according to claim 1, wherein the TSAHC further inhibits the differentiation and activation of hepatic epithelial cells or macrophages, glucose uptake, and glycolytic function activation.

3. The immunosuppressive method according to claim 1, wherein the cytokine or chemokine inhibits the increase of the expression of TM4SF5 or SIRT1 or the increase of the phosphorylation of FAK (Tyrosine 397), c-Src (Tyrosine 416), and STAT3 (Tyrosine 705) in hepatic epithelial cells.

4. The immunosuppressive method according to claim 1, wherein the cytokine or chemokine inhibits the recruit of immune cells into the liver tissue or the increase of the phosphorylation of FAK (Tyrosine 397), c-Src (Tyrosine 416), and STAT3 (Tyrosine 705) in hepatic epithelial cells, or the expression of collagen I alpha 1 or laminin γ2.

5. The immunosuppressive method according to claim 1, wherein the cytokine or chemokine interacts with macrophages to inhibit the expression of TM4SF5 in macrophages.

6. The immunosuppressive method according to claim 1, wherein the cytokine or chemokine is at least one selected from the group consisting of F4/80, IL1β, IL6, TNFα, CCR10, CXCL6, CCL2, CCL5, CCL20, CXCL1, CXCL2, CXCL3, CXCL5, CXCL6, CXCL8, and CXCL10.

7. The immunosuppressive method according to claim 1, wherein the cytokine or chemokine is at least one selected from the group consisting of CCL2, CCL5, CCL20, CXCL1, CXCL6, CXCL8, and CXCL10, that are increased by the TM4SF5 expression dependently or decreased by the Kelch Like ECH Associated Protein 1 (KEAP1) expression.

8. The immunosuppressive method according to claim 1, wherein the TSAHC reduces the secretion of at least one selected from the group consisting of IL-6, CCL2, IL1 ß and TNFα in macrophages.

9. The immunosuppressive method according to claim 1, wherein the TSAHC inhibits the binding of TM4SF5 and IL6Rα in hepatic epithelial cells.

10. The immunosuppressive method according to claim 1, wherein the TSAHC further inhibits the increase of oxygen consumption caused by mitochondrial respiration.

11. The immunosuppressive method according to claim 1, wherein the immunosuppressive method is effective for preventing or treating excess inflammatory response of the liver or the liver tissue due to the fat accumulation, hepatic epithelial cell damage, α-SMA (α-smooth muscle actin) expression increase, immune cell activation and concentration, Ccl20 or Cxcl10 expression, or collagen accumulation caused by high-fat diet, methionine-choline deficient diet, or $CCl_4$ treatment.

12. The immunosuppressive method according to claim 1, wherein the immunosuppressive method inhibits the increase of the expression of Tm4sf5, Trem2, Clec4f or Tim4 in Kupffer macrophages or bone marrow-derived macrophages caused by high-fat diet or methionine-choline-deficient diet.

* * * * *